(12) United States Patent
Dziubinski et al.

(10) Patent No.: US 10,262,111 B2
(45) Date of Patent: *Apr. 16, 2019

(54) SYSTEMS FOR SAFE AND REMOTE OUTPATIENT ECG MONITORING

(71) Applicant: MEDICALGORITHMICS S.A., Warsaw (PL)

(72) Inventors: Marek Dziubinski, Warsaw (PL); Ryszard Piotrowicz, Warsaw (PL); Ewa Piotrowicz, Warsaw (PL); Rafal Baranowski, Warsaw (PL)

(73) Assignee: MEDICALGORITHMICS S.A., Warsaw (PL)

( * ) Notice: Subject to any disclaimer, the term of this patent is extended or adjusted under 35 U.S.C. 154(b) by 0 days.

This patent is subject to a terminal disclaimer.

(21) Appl. No.: 15/808,956

(22) Filed: Nov. 10, 2017

(65) Prior Publication Data

US 2018/0089388 A1 Mar. 29, 2018

Related U.S. Application Data

(60) Continuation of application No. 15/143,281, filed on Apr. 29, 2016, now Pat. No. 9,846,764, which is a
(Continued)

(30) Foreign Application Priority Data

Oct. 14, 2005 (EP) .................................. 05077368

(51) Int. Cl.
*A61B 5/00* (2006.01)
*G06F 19/00* (2018.01)
(Continued)

(52) U.S. Cl.
CPC ........ *G06F 19/3418* (2013.01); *A61B 5/0006* (2013.01); *A61B 5/0022* (2013.01);
(Continued)

(58) Field of Classification Search
CPC .................................................. A61B 5/04012
(Continued)

(56) References Cited

U.S. PATENT DOCUMENTS 4,356,486 A 10/1982 Mount
4,407,288 A 10/1983 Langer et al.
(Continued)

FOREIGN PATENT DOCUMENTS

EP 1 473 667 A1 3/2004
WO WO 1993/022970 A1 11/1993
(Continued)

OTHER PUBLICATIONS

Zwickler et al., "Audio Engineering and Psychoacoustics: Matching Signals to the Final Receiver, the Human Auditory System;" Journal of the Audio Engineering Society, vol. 39, No. 3; Mar. 1, 1991; pp. 115-126.
(Continued)

*Primary Examiner* — Paula J Stice
(74) *Attorney, Agent, or Firm* — Daly, Crowley, Mofford & Durkee, LLP

(57) ABSTRACT

A system and method providing outpatient ECG monitoring and safe home based cardiac tele-rehabilitation. The system includes a recordation module for recording ECG signals using at least one lead, a tele-rehabilitation module for home based exercise management for a patient's recovery, the tele-rehabilitation module including a processing module for recognizing erroneous data from the ECG signals and an analysis module for calculating beat-to-beat annotations and determining if an ECG event and/or if a QT interval duration change has occurred. The system can include an exercise module for guiding the patient during an exercise session, a visual display that informs the patient to start and/or to stop the tele-rehabilitation exercise, a visual display and/or
(Continued)

audible signal that informs the patient of an incoming or a missed tele-rehabilitation exercise session, and/or a communication module for transmitting/receiving data between the a cardiac tele-rehabilitation module and a physician/monitoring center.

13 Claims, 15 Drawing Sheets

Related U.S. Application Data continuation of application No. 14/330,284, filed on Jul. 14, 2014, now Pat. No. 9,351,652, which is a division of application No. 12/090,183, filed on Apr. 14, 2008, now Pat. No. 8,818,496, which is a continuation of application No. PCT/PL2006/000068, filed on Oct. 16, 2006.

(60) Provisional application No. 60/987,192, filed on Nov. 12, 2007, provisional application No. 60/987,180, filed on Nov. 12, 2007, provisional application No. 60/987,043, filed on Nov. 10, 2007, provisional application No. 60/986,761, filed on Nov. 9, 2007, provisional application No. 60/948,527, filed on Jul. 9, 2007.

(51) Int. Cl.
*A61B 5/0452* (2006.01)
*A61B 5/0464* (2006.01)
*A61B 5/0472* (2006.01)
*A61B 5/04* (2006.01)
*A61B 5/0432* (2006.01)
*A61B 5/0468* (2006.01)
*A61B 5/11* (2006.01)

(52) U.S. Cl.
CPC ........ *A61B 5/04012* (2013.01); *A61B 5/0432* (2013.01); *A61B 5/0452* (2013.01); *A61B 5/0464* (2013.01); *A61B 5/0468* (2013.01); *A61B 5/0472* (2013.01); *A61B 5/1118* (2013.01); *A61B 5/4833* (2013.01); *A61B 5/7203* (2013.01); *A61B 5/7264* (2013.01); *A61B 5/742* (2013.01); *A61B 5/7405* (2013.01); *G06F 19/00* (2013.01); *G06F 19/3481* (2013.01)

(58) Field of Classification Search
USPC .................................................. 600/509–528
See application file for complete search history.

(56) References Cited

U.S. PATENT DOCUMENTS

| | | |
|---|---|---|
| 4,531,527 A | 7/1985 | Reinhold, Jr. et al. |
| 4,572,182 A | 2/1986 | Royse |
| 4,622,979 A | 11/1986 | Katchis et al. |
| 4,763,663 A | 8/1988 | Uphold et al. |
| 4,803,625 A | 2/1989 | Fu et al. |
| 4,889,131 A | 12/1989 | Salem et al. |
| 4,916,441 A | 4/1990 | Gombrich |
| 4,938,228 A | 7/1990 | Righter et al. |
| 4,958,641 A | 9/1990 | Digby et al. |
| 4,967,756 A | 11/1990 | Hewitt |
| 4,977,899 A | 12/1990 | Digby et al. |
| 5,003,984 A | 4/1991 | Muraki et al. |
| 5,012,814 A | 5/1991 | Mills et al. |
| 5,012,815 A | 5/1991 | Bennett, Jr. et al. |
| 5,024,225 A | 6/1991 | Fang |
| 5,033,474 A | 7/1991 | Varelis et al. |
| 5,111,396 A | 5/1992 | Mills et al. |
| 5,128,552 A | 7/1992 | Fang et al. |
| 5,191,891 A | 3/1993 | Righter |
| 5,226,425 A | 7/1993 | Righter |
| 5,238,001 A | 8/1993 | Gallant et al. |
| D341,659 S | 11/1993 | Homayoun et al. |
| 5,289,824 A | 3/1994 | Mills et al. |
| 5,304,186 A | 4/1994 | Semler et al. |
| 5,307,818 A | 5/1994 | Segalowitz |
| 5,317,269 A | 5/1994 | Mills et al. |
| 5,319,363 A | 6/1994 | Weltch et al. |
| 5,333,616 A | 8/1994 | Mills et al. |
| 5,351,695 A | 10/1994 | Mills et al. |
| 5,365,935 A | 11/1994 | Righter et al. |
| 5,381,804 A | 1/1995 | Shambroom |
| 5,417,222 A | 5/1995 | Dempsey et al. |
| 5,441,047 A | 8/1995 | David et al. |
| 5,467,773 A | 11/1995 | Bergelson et al. |
| D372,785 S | 8/1996 | Sabri et al. |
| 5,573,506 A | 11/1996 | Vasko |
| 5,581,369 A | 12/1996 | Righter et al. |
| D377,983 S | 2/1997 | Sabri et al. |
| 5,609,156 A | 3/1997 | Keith et al. |
| 5,630,710 A | 5/1997 | Tune et al. |
| 5,631,495 A | 5/1997 | Dunn et al. |
| 5,687,717 A | 11/1997 | Halpern et al. |
| 5,704,364 A | 1/1998 | Saltzstein et al. |
| 5,730,143 A | 3/1998 | Schwarzberg |
| 5,738,104 A | 4/1998 | Lo et al. |
| 5,749,367 A | 5/1998 | Gamlyn et al. |
| 5,752,976 A | 5/1998 | Duffin et al. |
| 5,819,007 A | 10/1998 | Elghazawi |
| 5,885,245 A | 3/1999 | Lynch et al. |
| 5,931,791 A | 8/1999 | Saltzstein et al. |
| 5,941,829 A | 8/1999 | Saltzstein et al. |
| 5,959,529 A | 9/1999 | Kail |
| D414,870 S | 10/1999 | Saltzstein et al. |
| 5,983,127 A | 11/1999 | dePinto |
| D427,315 S | 6/2000 | Saltzstein et al. |
| D429,336 S | 8/2000 | Francis et al. |
| 6,171,237 B1 | 1/2001 | Avitail et al. |
| 6,225,901 B1 | 5/2001 | Kail |
| 6,366,871 B1 | 4/2002 | Geva |
| 6,416,471 B1 | 7/2002 | Kumar et al. |
| 6,466,806 B1 | 10/2002 | Geva et al. |
| 6,486,779 B1 | 11/2002 | Alroy |
| 6,537,233 B1 | 3/2003 | Rangayyan et al. |
| 6,569,095 B2 | 5/2003 | Eggers |
| 6,664,893 B1 | 12/2003 | Eveland et al. |
| 6,665,385 B2 | 12/2003 | Rogers et al. |
| 6,694,177 B2 | 2/2004 | Eggers et al. |
| 6,801,137 B2 | 10/2004 | Eggers |
| 6,871,089 B2 | 3/2005 | Korzinov et al. |
| 6,940,403 B2 | 9/2005 | Kail |
| 6,957,107 B2 | 10/2005 | Rogers et al. |
| 7,002,468 B2 | 2/2006 | Eveland et al. |
| 7,099,715 B2 | 8/2006 | Korzinov et al. |
| 7,130,396 B2 | 10/2006 | Rogers et al. |
| 7,194,300 B2 | 3/2007 | Korzinov |
| 7,212,850 B2 | 5/2007 | Prystowsky et al. |
| 7,222,054 B2 | 5/2007 | Geva |
| 7,266,405 B1 | 9/2007 | Alroy et al. |
| 7,299,159 B2 | 11/2007 | Nanikashvili |
| 7,374,545 B2 | 5/2008 | Alroy |
| 8,131,354 B2 * | 3/2012 | Arad (Abboud) ... A61B 5/0536 600/428 |
| 8,818,496 B2 | 8/2014 | Dziubinski et al. |
| 9,351,652 B2 | 5/2016 | Dziubinski et al. |
| 9,846,764 B2 | 12/2017 | Dziubinski et al. |
| 2001/0029338 A1 | 10/2001 | Krishnamachari |
| 2002/0032387 A1 | 3/2002 | Geva et al. |
| 2002/0067256 A1 | 6/2002 | Kail |
| 2002/0198473 A1 | 12/2002 | Kumar et al. |
| 2003/0028442 A1 | 2/2003 | Wagstaff et al. |
| 2003/0176795 A1 | 9/2003 | Harris |
| 2003/0187363 A1 | 10/2003 | Alroy |
| 2004/0102683 A1 | 5/2004 | Khanuja et al. |
| 2004/0122294 A1 | 6/2004 | Hatlestad |
| 2004/0260189 A1 | 12/2004 | Eggers et al. |
| 2005/0119580 A1 | 6/2005 | Everland |

(56) References Cited

U.S. PATENT DOCUMENTS

| | | |
|---|---|---|
| 2005/0171448 A1 | 8/2005 | Korzinov et al. |
| 2005/0203349 A1* | 9/2005 | Nanikashvili ........ A61B 5/0002 600/300 |
| 2006/0084881 A1 | 4/2006 | Korzinov et al. |
| 2006/0155203 A1 | 7/2006 | Munk |
| 2007/0015973 A1 | 1/2007 | Nanikashvili |
| 2007/0033072 A1* | 2/2007 | Bildirici .............. G06F 19/3418 705/3 |
| 2007/0129642 A1 | 6/2007 | Korzinov |
| 2007/0130657 A1 | 6/2007 | Roggers et al. |
| 2007/0156054 A1 | 7/2007 | Korzinov et al. |
| 2007/0219453 A1 | 9/2007 | Kremliovsky et al. |
| 2007/0288067 A1 | 12/2007 | Eveland |
| 2007/0293776 A1 | 12/2007 | Korzinov et al. |

FOREIGN PATENT DOCUMENTS

| | | |
|---|---|---|
| WO | WO 2001/093758 A1 | 12/2001 |
| WO | WO 2005/006209 A1 | 1/2005 |
| WO | WO 2007/043903 A1 | 4/2007 |

OTHER PUBLICATIONS

Brusco et al., "Digital Phonocardiography: a PDA-Based Approach;" 26th Annual International Conference of the IEEE Engineering in Medicine and Biology Society, vol. 3; Jan. 2004; pp. 229-2302.

Erickson et al., "In-Vitro Study of Mechanical Heart Valve Sound Loudness as Measure by ISO-532/B;"Proceedings of IEEE Seventh Symposium on Computer-Based Medical Systems; Jan. 1994; 2 Pages.

PCT International Search Report dated Jun. 21, 2007 for International Appl. No. PCT/PL2006/000067.

PCT International Search Report dated Feb. 26, 2007 for International Appl. No. PCT/PL2006/000068.

Prasad et al., "Classification of ECG Arrhythmias Using Multi-Resolution Analysis and Neural Networks;" IEEE TENCON 2003—Conference on Technologies for the Asia-Pacific Region, vol. IV; Oct. 15-17, 2003; Bangalore, India, pp. 227-231.

European Examination Report dated Dec. 13, 2016 for European Application No. 06812860.2; 8 Pages.

Response (with Amended Claims) to European Examination Report dated Dec. 13, 2016 for European Application No. 06812860.2; Response filed Jun. 22, 2017; 10 Pages.

Second European Examination Report dated Sep. 26, 2017 for European Application No. 06812860.2; 6 Pages.

Response (with Amended Claims) to Second European Examination Report dated Sep. 26, 2017 for European Application No. 06812860.2; Response filed Apr. 5, 2018; 10 Pages.

Third European Examination Report dated Jun. 25, 2018 for European Application No. 06812860.2; 5 Pages.

Response (with Amended Claims) to European Office Action dated Jun. 25, 2018 for European Application No. 06812860.2; Response filed Oct. 26, 2018; 13 Pages.

* cited by examiner

SYSTEMS FOR SAFE AND REMOTE OUTPATIENT ECG MONITORING

CROSS-REFERENCE TO RELATED APPLICATION(S)

This application is a Continuation of U.S. application Ser. No. 15/143,281, filed on Apr. 29, 2016, and entitled, "Systems for Safe and Remote Outpatient ECG Monitoring," now U.S. Pat. No. 9,846,764, issued on Dec. 19, 2017. U.S. application Ser. No. 15/143,281 is a Continuation of U.S. application Ser. No. 14/330,284, filed on Jul. 14, 2014, and entitled, "Systems for Safe and Remote Outpatient ECG Monitoring," now U.S. Pat. No. 9,351,652, issued on May 31, 2016. U.S. application Ser. No. 14/330,284 is a Divisional of U.S. application Ser. No. 12/090,183, filed on Apr. 14, 2008, now U.S. Pat. No. 8,818,496, issued on Aug. 26, 2014. U.S. application Ser. No. 12/090,183 claims the benefit of U.S. Provisional Application No. 60/987,192, filed on Nov. 12, 2007, U.S. Provisional Application No. 60/987,180, filed on Nov. 12, 2007, U.S. Provisional Application No. 60/987,043, filed on Nov. 10, 2007, U.S. Provisional Application No. 60/986,761, filed on Nov. 9, 2007, Polish Patent Application No. P383243, filed on Sep. 2, 2007, entitled "A system for remote cardiac rehabilitation" (English translation), U.S. Provisional Application No. 60/948,527, filed on Jul. 9, 2007, and is a continuation of International Application No. PCT/PL2006/000068, filed on Oct. 16, 2006, published in English, which claims priority to EP Application No. 05077368.8, filed Oct. 14, 2005. The entire teachings of each of the above applications are incorporated herein by reference.

BACKGROUND

Automated analysis of digitized electrocardiogram (ECG) signals has various applications. Algorithms operating in real-time with the ability to deal with lead limited signals are useful in external defibrillators and lead-limited monitoring systems. They can be also used, as described here, in long-term ECG telemetry applications.

In the case of a lead limited ECG, it is difficult to automatically distinguish between normal QRS complexes and pathological ECG peaks representing ventricular contractions. Usually pathological complexes are significantly wider and have larger amplitude than normal QRS complexes; however in some cases the situation may be the opposite. A decrease in the number of leads causes the number of misinterpreted events to increase due to a stronger influence of noise and parasite impulses in the signal. In a single lead analysis, it is extremely difficult to distinguish between parasite peaks and QRS complexes due to the lack of additional leads, which are typically used for reference or comparison.

SUMMARY

There is provided a system and method providing outpatient ECG monitoring and safe home based cardiac tele-rehabilitation, even for patients with high risk of another infarcts. The system includes a recordation module for recording ECG signals using at least one lead, a cardiac tele-rehabilitation module for home based exercise management for a patient's recovery from a heart disease, the cardiac tele-rehabilitation module including a processing module for recognizing erroneous data from the ECG signals and an analysis module for calculating beat-to-beat annotations and determining if an ECG event has occurred and/or if a QT interval duration change has occurred, and a communication module for reporting the processed ECG signals and/or other detected ECG events including streaming all of the annotations and information describing each ECG beat. The system can also include an exercise module for guiding the patient during an exercise session, a visual display that informs the patient to start and/or to stop the tele-rehabilitation exercise, a visual display and/or audible signal that informs the patient of an incoming or a missed tele-rehabilitation exercise session, and/or a communication module for transmitting/receiving data between the a cardiac tele-rehabilitation module and a physician/monitoring centre.

In some embodiments, the information provided to the patient can include an indication to intensify the exercise because the patient's heart rate is below a predefined threshold, an indication to decrease the exercise intensity because the patient's heart rate is above a predefined threshold, an indication to stop the exercise because a significant cardiac event has occurred, and an indication to contact the patient's physician.

In some embodiments, the physician/monitoring centre can include a control module for controlling/reprogramming the cardiac tele-rehabilitation module. The control module, such as a computer, can allow the patient's physician, or a medical personnel assign to the patient, to control the patient's tele-rehabilitation exercise session. The control of the tele-rehabilitation exercise session can be based on reviewing received data from the cardiac tele-rehabilitation module, the received data including an ECG analysis of the patient and a data describing the patient's physical and mental condition. In some embodiments, the data describing patient's physical and mental condition include a blood pressure of the patient, a body weight of the patient, a stress information of the patient; a mood information of the patient, and a pharmacotherapy information of the patient. In some embodiments, the data describing patient's physical and mental condition can be input into the cardiac tele-rehabilitation module by the patient, by external measuring devices, and/or a person at the physician/monitoring centre.

In some embodiments, the control module can allow for setting or modifying the tele-rehabilitation program. The settings or modifications can include a minimum heart rate exercise threshold, a maximum heart rate exercise threshold, a number of exercise sessions during the day, a session duration, a number of exercises during each session, and exercise and pause duration.

In some embodiments, a communication module is used for communicating the processed ECG signals and/or other detected ECG event. The detected ECG event can be reported to medical personnel or a wearer of the recordation module. The processed ECG signals can be segmented and then reported to medical personnel.

In some embodiments, a server can be used for receiving the processed ECG signals and/or the ECG event from the reporting module. The server can receive the processed ECG signals and/or the ECG event from the reporting module for a plurality of patients. The server can direct the processed ECG signals and/or the ECG event from the reporting module for the plurality of patients to medical personnel responsible for a respective patient. The medical personnel can have direct access to a patient's processing module and/or analysis module through the server. The direct access can allow the medical personnel to remotely alter parameters stored in the patient's processing module and/or analysis module.

In some embodiments, the processing module can include an analysis algorithm recognizing erroneous data from the ECG signals. The analysis algorithm can include a noise and distortion detection sub-algorithm (NDDA) for detecting noisy and non-linearly distorted ECG fragments including detecting distortions produced by not properly attached, to the patient's body, electrodes. The NDDA can further estimate a broad band noise energy level of the signal.

A method for analyzing limited-lead electrocardiogram (ECG) system signals, includes recording ECG signals using at least one lead, performing cardiac tele-rehabilitation, wherein performing cardiac tele-rehabilitation includes recognizing erroneous data from the ECG signals to form a pre-classified ECG signal and determining if an ECG event has occurred from the pre-classified signal and calculating annotations for every ECG beat.

The method can further include reporting the calculated annotations for every ECG beat and/or the ECG event. The ECG event can be reported to medical personnel or a wearer of the recordation module. The calculated annotations representing each ECG beat can be segmented and then reported to medical personnel.

In some embodiments, the method can further include receiving the annotations for each ECG beat and/or the ECG event at a remote location. The erroneous data from the ECG signals can be detected using an analysis algorithm. The analysis algorithm can include a noise and distortion detection sub-algorithm (NDDA) for detecting noisy and non-linearly distorted ECG fragments. The NDDA can further estimate a broad band noise energy level of the signal and detect distortions generated by not properly attached electrodes. The pre-classified signal can be analyzed using a beat classification algorithm and/or an arrhythmia detection algorithm. The analyzed signal can be verified using a detection evaluation correction algorithm. The beat classification algorithm and the arrhythmia detection algorithm can generate the calculated annotations for every ECG beat.

In some embodiments, the method can further include updating an averaged normal ECG period for each new non-pathological ECG period based on the performed beat classification and arrhythmia detection. The averaged ECG period can be used for calculating ST segment elevation and for QT interval duration difference between the averaged ECG period and the reference ECG period. The reference ECG period can be an averaged ECG period with a predetermined QT interval, allowing for QT interval determination of each new averaged ECG period based on the predetermined interval value and the current QT interval difference value. The QT interval difference is obtained by finding a best match of a time domain shifted T wave representation signal of the averaged ECG period and the T wave representation signal of the reference ECG period. The signal representations can be difference signals of the averaged ECG period and the reference ECG period. The best match of the time domain shifted T wave representation of the averaged ECG period and the T wave representation of the reference ECG period can be the maximum value of a shifted T wave matching function. The index of the maximum value of a similarity function can be interpolated to enhance the T wave shift accuracy. The interpolation can be performed by a parabola fitting to the maximum similarity value and a surrounding values of the similarity curve. The maximum similarity value can be the maximum of all maximum similarity values of the reference ECG period and all collected auxiliary reference ECG periods compared with a new averaged ECG period. The auxiliary reference ECG periods can be collected if a shape changing T wave occurs. The averaged ECG period collected can be used as an auxiliary reference ECG period.

In some embodiments, a non-pathological ECG period can be a current ECG period used for calculating a T wave alternans amplitude. A value of the base line level can be a median value of an isoelectric line signal segment preceding a current ECG period. The value of a base line level deviation can be a standard deviation of the current base line level and a J preceding base line level. The value of the isoelectric line deformation of the current ECG period can be a standard deviation of a difference of the current isoelectric line, preceding the current ECG period and an isoelectric line preceding the previous ECG period.

In some embodiments, an unbiased current ECG period can be calculated by removing a low frequency T wave shape trend from the current ECG period. The low frequency T trend can be removed by subtracting an averaged ECG period from the current ECG period.

In some embodiments, a periodicity values representing each sample of the current ECG period can be calculated. The periodicity values for n samples of the current ECG period can be calculated based on n autocorrelation sequences, calculated with the use of a J consecutive unbiased ECG periods, including the current unbiased ECG period. A T wave amplitude can be calculated based on an unbiased-averaged-difference-ECG-period. The unbiased-averaged-difference-ECG-period can be calculated based on J/2 pairs of a J consecutive unbiased ECG periods, the preceding the current unbiased ECG period and including the current unbiased ECG period. The T wave alternans can be a maximum of the unbiased-averaged-difference-ECG-period. An unbiased-averaged-difference-ECG-period can be weighted by the periodicity values. A maximum value of the unbiased-averaged-difference-ECG-period, weighted by periodicity values and compensated by base line drift deviation values and isoelectric line deformation values can be a calculated T wave alternans amplitude for the current ECG period.

The system and methods provide a real-time and long-term outpatient ECG monitoring system with real-time and remote access to the monitoring results. The methods and systems allow for decentralized, in terms of patient location, QT interval monitoring studies with remote access to the ECG analysis devices and analysis results. Remote access to the real-time data allows for controlling the study from any location. Real-time access to the monitoring devices, and the methodology allows for controlling and correcting the QT/QTc interval measurements in very efficient manner, and allows for processing large amounts of data (long-term monitoring periods, many patients at the same time) simultaneously by a single operator.

Analysis of a lead-limited ECG is extremely difficult because the signals contain a large number of ambiguities, i.e., signals from various patients may be very substantially different. When disturbances occur in these signals, it is easy to confuse parasite impulses or peaks with the impulses generated by the heart. In addition, such analysis, by definition, provides limited amount of information in comparison to a typical 12 lead ECG.

The present systems and methods provide for lead-limited ECG signal analysis having the ability to automatically detect QRS complexes, classify the detected beats, identify heart arrhythmias and ST segment elevation events. Identifying these elements is necessary to perform robust and efficient automated QT interval measurements. Real-time processing is important in case of long-term monitoring intervals, where it is necessary to instantly access the QT interval changes.

In addition, based on a real-time analysis produced by the device carried by the patient, the systems can be used for remote home tele-rehabilitation, where intensity of the exercised performed by the patient is controlled by the device, based on a calculated in real-time heart rate. Since the system sends the analysis results all the time (24 hours a day) also including the rehabilitation session, the heart condition of the patient is constantly monitored and therefore the rehabilitation process is safe. In case of detecting abnormalities in the ECG signal in real-time the patient is informed to stop the exercise and to contact a medical personnel. As described above, the system provides possibility of constant, beat-to-beat monitoring of the patient's ECG, where automatically selected ECG strips plus annotations of every beat are transmitted to the physician responsible for controlling the rehabilitation progress.

Constant monitoring during the day and during the night is of importance, because certain ECG based predictors allow to determine possibility of potential future problems. The predictors are presence of certain arrhythmias, ST segment elevation changes, QT/QTc interval changes, T wave alternas amplitude. The system allows for detection of all of the mentioned parameters in real-time. Moreover, the patient, before starting the exercise session is obliged to provide information describing his/her physical and mental condition. This data, along with the automatically detected ECG findings is remotely transmitted to the monitoring centre for analysis. Only in case of positive evaluation of the mentioned data, the patient is allowed to exercise. The exercise guiding software is remotely triggered by the physician from the monitoring centre.

Analysis of a lead-limited ECG is a difficult task, because the signals contain a large number of ambiguities, i.e., signals from various patients may be very substantially different. When disturbances occur in these signals, it is easy to confuse parasite impulses or peaks with the impulses generated by the heart. In addition, such analysis, by definition, provides limited amount of information in comparison to a typical 12 lead ECG. Therefore, the lead-limited ECG analysis presents a greater challenge from an algorithmic point of view.

The present systems and methods provide for lead-limited ECG signal analysis having the ability to automatically detect QRS complexes, classify the detected beats, identify heart arrhythmias, calculate ST segment elevation, calculate QT interval duration and T wave alternans (TWA) amplitude. Identifying these elements is useful in determining the patient's heart condition and useful in predicting potential problems.

BRIEF DESCRIPTION OF THE DRAWINGS

The foregoing and other objects, features and advantages will be apparent from the following more particular description of embodiments, as illustrated in the accompanying drawings in which like reference characters refer to the same parts throughout the different views. The drawings are not necessarily to scale, emphasis instead being placed upon illustrating the principles of the embodiments.

DETAILED DESCRIPTION

In general, there is provided a real-time and long-term outpatient ECG monitoring system with real-time and remote access for the monitoring results. On one hand the system can be viewed as a remote real-time holter system, where an analysis report, very much similar to the holter report, can be generated, but on the other hand the system works in real-time and transmits the analysis results from the patient, over a network, such as the internet and/or a mobile telecommunication network, to physician, or monitoring personnel who can immediately access the data.

An electrocardiogram (ECG) is a graphical display produced by an electrocardiograph, which records the electrical activity of the heart over time. The graphical display is a series of electrical phenomena resulting from a trial and ventricular depolarization and repolarization of the heart muscle.

Figure 1:
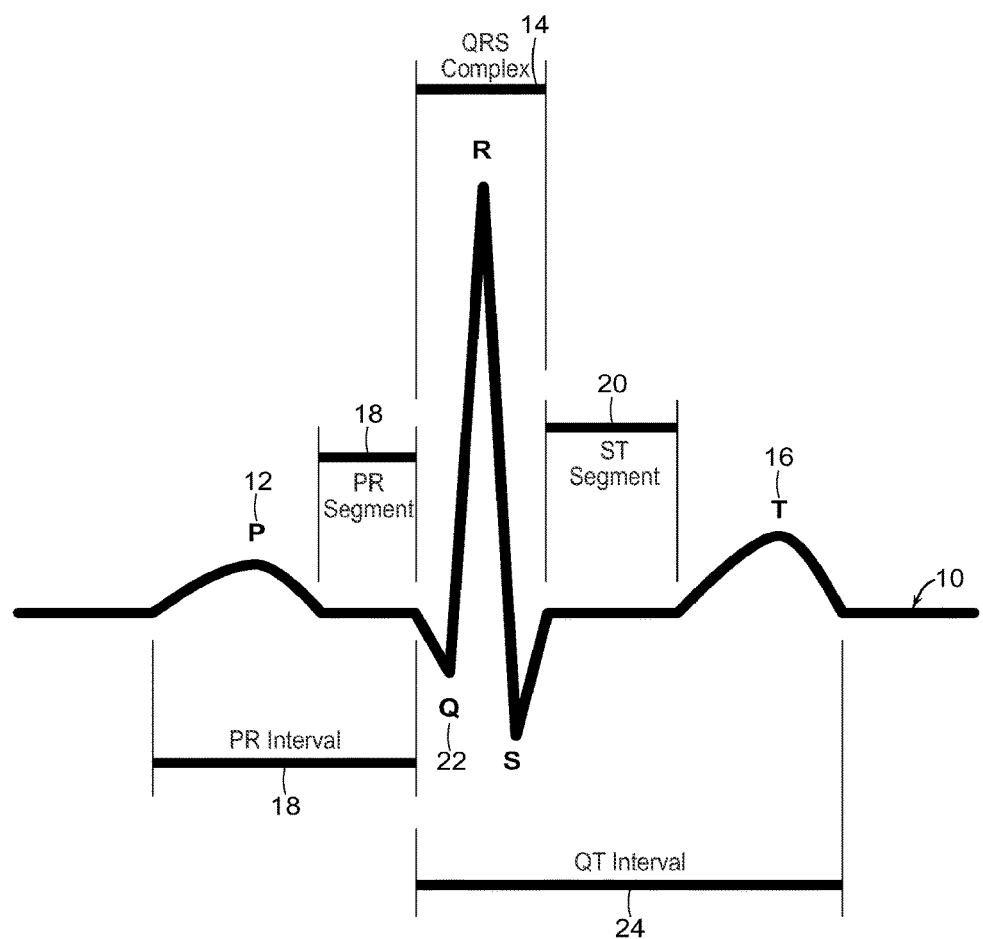
FIG. 1 is an illustration of a waveform output from an electrocardiogram (ECG) (for a single cardiac cycle)

FIG. 1 represents single cardiac cycle (single heart beat), with a description of ECG peaks, waves and an intervals, which are the basis of ECG analysis and classification. A typical ECG tracing 10 of a normal heartbeat (or cardiac cycle) consists of a P wave 12, a QRS complex 14 and a T wave 16. A small U wave (not shown) is normally visible in 50 to 75% of ECGs. The baseline voltage of the electrocardiogram is known as an isoelectric line. Typically, the isoelectric line is measured as the portion of the tracing following the T wave 16 and preceding the next P wave 12.

The P Wave 12 is seen during normal a trial depolarization, a mean electrical vector is directed from the SA node towards the AV node, and spreads from the right atrium to the left atrium. The relationship between P waves 12 and QRS complexes 14 helps distinguish various cardiac arrhythmias. For example, the shape and duration of the P waves 12 may indicate a trial enlargement.

The PR segment (interval) 18 is measured from the beginning of the P wave 12 to the beginning of the QRS complex 14. The PR interval 18 is usually 120 to 200 ms long. On an ECG tracing, this corresponds to 3 to 5 small boxes. A prolonged PR interval 18 may indicate a first degree heart block; a short PR interval 18 may indicate a pre-excitation syndrome via an accessory pathway that leads to early activation of the ventricles, such as seen in Wolff-Parkinson-White syndrome; a variable PR interval 18 may indicate other types of heart block; a PR interval 18 depression may indicate a trial injury or pericarditis; and variable morphologies of P waves 18 in a single ECG lead is suggestive of an ectopic pacemaker rhythm, such as wandering pacemaker or multifocal a trial tachycardia.

The QRS complex 14 is a structure on the ECG that corresponds to the depolarization of the ventricles. Because the ventricles contain more muscle mass than the atria, the QRS complex 14 is larger than the P wave 12. In addition, because the His-Purkinje system coordinates the depolarization of the ventricles, the QRS complex 14 tends to look "spiked" rather than rounded due to the increase in conduction velocity. A normal QRS complex 14 is 0.06 to 0.10 sec (60 to 100 ms) in duration. The duration, amplitude, and morphology of the QRS complex 14 is useful in diagnosing cardiac arrhythmias, conduction abnormalities, ventricular hypertrophy, myocardial infarction, electrolyte derangements, and other disease states. Q waves 22 can be normal (physiological) or pathological.

The ST segment 20 connects the QRS complex 14 and the T wave 16 and has a duration of 0.08 to 0.12 sec (80 to 120 ms). The ST segment 20 starts at a J point (junction between the QRS complex 14 and ST segment 20) and ends at the beginning of the T wave 16. However, since it is usually difficult to determine exactly where the ST segment 20 ends and the T wave 16 begins, the relationship between the ST segment 20 and T wave 16 are typically examined together. The typical ST segment 20 duration is usually around 0.08 sec (80 ms). It should be essentially level with the PR segment 18 and TP segment (not shown). A normal ST segment 20 has a slight upward concavity. Flat, downsloping, or depressed ST segments 20 may indicate coronary ischemia, while elevated ST segment 20 may indicate myocardial infarction.

The T wave 16 represents the repolarization (or recovery) of the ventricles. The interval from the beginning of the QRS complex 14 to the apex of the T wave 16 is referred to as the absolute refractory period. The last half of the T wave 16 is referred to as the relative refractory period (or vulnerable period). Inverted (or negative) T waves 16 can be a sign of coronary ischemia, Wellens' syndrome, left ventricular hypertrophy, or CNS disorder. Tall or "tented" symmetrical T waves 16 may indicate hyperkalemia. Flat T waves 16 may indicate coronary ischemia or hypokalemia.

The QT interval 24 is measured from the beginning of the QRS complex 14 to the end of the T wave 16. A normal QT interval 24 is usually about 0.40 seconds. The QT interval 24 as well as the corrected QT interval 24 are important in the diagnosis of long QT syndrome and short QT syndrome and also are important in ventricular tachyarrhythmia prediction.

The U wave is typically small, and not always seen, and by definition, follows the T wave 16. U waves are thought to represent repolarization of the papillary muscles or Purkinje fibers. Prominent U waves are most often seen in hypokalemia, but may be present in hypercalcemia, thyrotoxicosis, or exposure to digitalis, epinephrine, and Class 1A and Class 3 antiarrhythmics, as well as in congenital long QT syndrome and in the setting of intracranial hemorrhage. An inverted U wave may represent myocardial ischemia or left ventricular volume overload.

T-wave alternans (TWA) is a non-invasive test of the heart that is used to identify patients who are at increased risk of sudden cardiac death. It is most often used in patients who have had myocardial infarctions (heart attacks) or other heart damage to see if they are at high risk of developing a potentially lethal cardial arrhythmia. Those patients who are found to be at high risk would therefore benefit from the placement of a defibrillator device which can stop an arrhythmia and save the patient's life.

The TWA test uses an electrocardiogram (ECG) measurement of the heart's electrical conduction. The test looks for the presence of repolarization alternans (T-wave alternans), which is a variation in the vector and amplitude of the T-wave component of the ECG. The amount of variation is small, on the order of microvolts, so sensitive digital signal processing techniques are required to detect TWA.

TWA were first described in 1908, and at that time when sensitive digital techniques were not available, only large variation ("macroscopic" TWA) could be detected. Those large TWAs were associated with increased susceptibility to lethal ventricular tachyarrhythmias.

Figure 2:
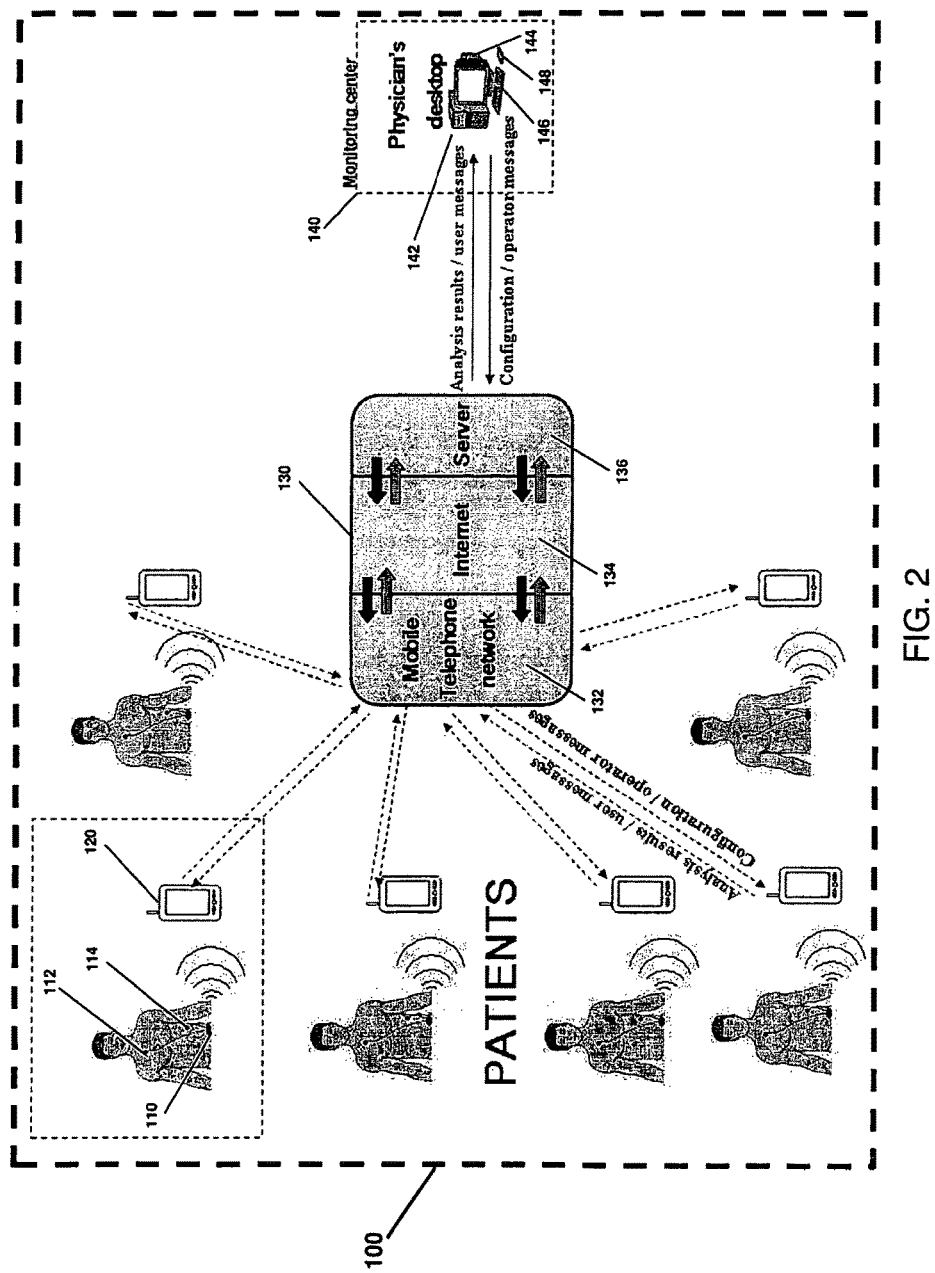
FIG. 2 is an illustration of a system diagram for monitoring patients from remote locations.

FIG. 2 is an illustration of the system 100 diagram for provide remote outpatient cardiac tele-rehabilitation and a long-term ECG monitoring. The system 100 also provides real-time and automated QRS detection, beat classification, ECG arrhythmia detection, ST segment elevation monitoring, QT interval duration monitoring and TWA amplitude monitoring. Monitoring of these elements is necessary for remote tele-rehabilitation control and allows for predicting potential heart functionality problems. The system 100 includes, but is not limited to, a recordation module 110, a cardiac tele-rehabilitation module 120, and data transmission network 130, and a remote monitoring module 140.

The recordation module 110 can be an ECG digitization and wireless transmission device, such as a Bluetooth device, for recording ECG signals using at least one lead (112, 114). The recordation device 110 operates on signal from a first electrode 112 and a second electrode 114 (single channel or single lead) or three or more electrodes (multi channel or multi-lead).

The tele-rehabilitation module 120 provides real-time ECG monitoring while recognizing erroneous signals from the ECG signals; real-time control of tele-rehabilitation exercise duration; pause insertion to separate exercise duration; exercise intensity; and a two-way data communication channel between a patient and a physician. Prior to system 100 operation, the patient inputs patient information, not discernible by the system 100, into the tele-rehabilitation module 120. The patient information can include patient body weight, blood pressure, patient mood data, and patient pharmacotherapy related information.

In operation, the tele-rehabilitation module 120, in conjunction with the recordation module 110, acquires ECG analysis related information and guides the patient though an exercise or series of exercises. The data received by the tele-rehabilitation module 120 is analyzed to determine the patient state. For example, if the tele-rehabilitation module 120 detects a heart rate above or below a predefined threshold, it informs the patient to intensify or the exercise. If the patient state is normal, the tele-rehabilitation module 120 indicates the patient can continue the tele-rehabilitation exercise/program. If a potential threat is detected, the tele-rehabilitation module 120 indicates the patient to stop the tele-rehabilitation exercise/program and/or contact the monitoring centre 140 for further instructions. The telerehabilitation module 120 also forwards all the gathered information to the physician/monitoring centre 140 through the data transmission network 130. The gathered information includes patient body weight, patient stress data, patient mood data, and patient pharmacotherapy related information, blood pressure, and the ECG analysis related information.

The remote monitoring module or physician/monitoring centre 140 can include a desktop computer 142, having various computer periphery devices, such as a monitor 144, a keyboard 146, and a mouse 148. The remote monitoring module 130 can include software for ECG visualization; editing/configuring the remote ECG analysis algorithm configuration; editing/configuring the remote tele-rehabilitation exercise/program; and controlling the tele-rehabilitation progress.

The data transmission network 130 can include a mobile telephone network 132, internet backbone 134, computer servers 136, or a combination thereof, or like devices, to facilitate data transmission between the tele-rehabilitation module 120 and the remote monitoring module 140. The servers 146 can include software for data management and communication between the tele-rehabilitation module 120 and the remote monitoring module 140. It should be understood any type of data transmission network can be used to facilitate the data transmission between the tele-rehabilitation module 120 and the remote monitoring module 140.

Figure 3:
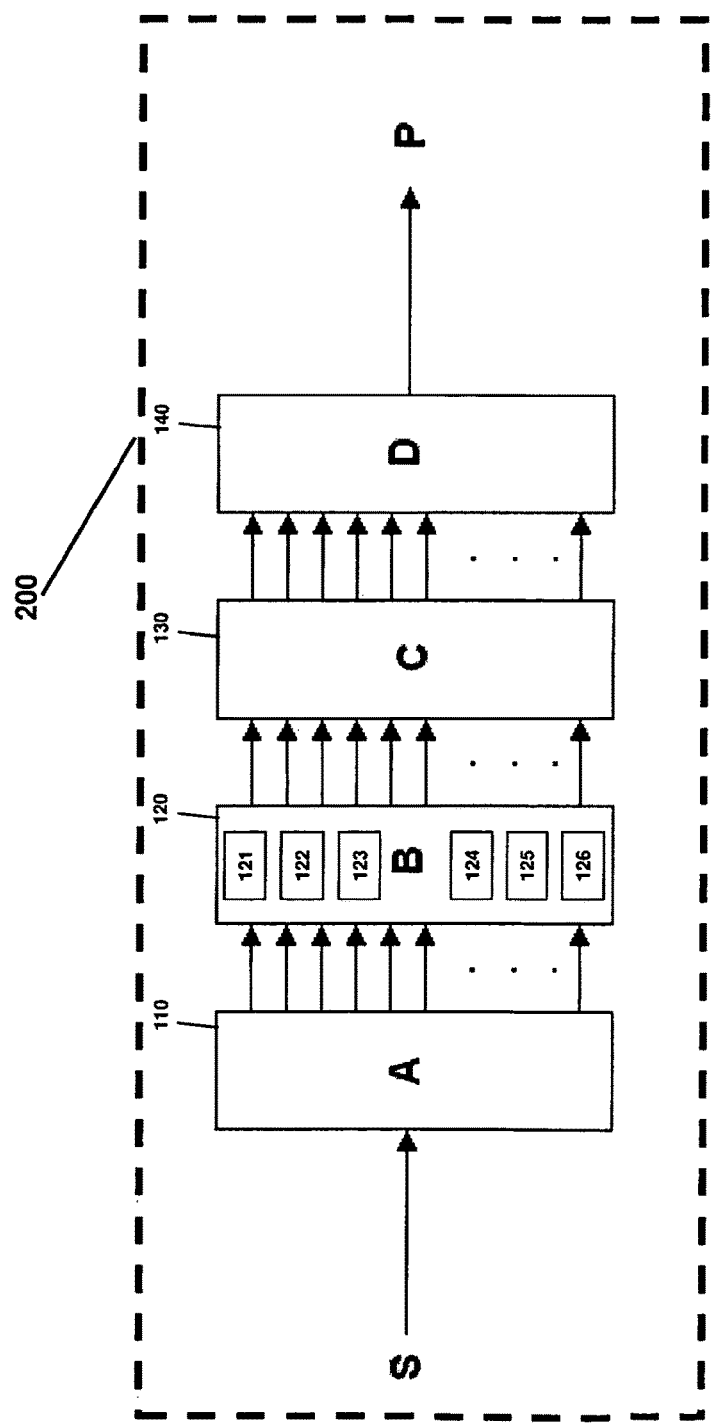
FIG. 3 is a schematic illustration of the system of FIG. 2.

FIG. 3 represents a schematic representation 200 of the system 100 of FIG. 2. The system 100 includes the recordation module 110, the cardiac tele-rehabilitation module 120, and the data transmission network 130, and the remote monitoring module 140.

The recordation module 110 can be an ECG digitization and transmission unit operable on two (2) electrodes (single channel), or three (3) electrodes (multi channel).

The tele-rehabilitation module 120 can include a processing module 121, an analysis module 122, an exercise module 123, a visual display 124, an audible device 125, and a communication/reporting module 126.

In some embodiments, the tele-rehabilitation module 120 can be a touch screen type device, such as a personal digital assistant (PDA) or SmartPhone. The processing module 121 can be a microcomputer, processor, or any other known type device. It should be understood that the processing module 121 includes a memory storage device. The analysis module 122 can be software operable on processing module 121. The exercise module 123 can be further software operable on processing module 121, or part of, or a sub-component of, the analysis module 122, or any combination thereof. The visual display 124 can be a type-screen type display, or any other known type device. The audible device 125 can be a speaker, or any other known type device. The communication/reporting module 126 can be a GSM phone module, a CMDA phone module, a TDMA phone module, or the like for transmitting/receiving data information between the cardiac tele-rehabilitation module 120 and the remote monitoring module 140.

The system 100 manages a tele-rehabilitation program for a patient and monitors an ECG signal in real-time, at any location of the patient. In addition, once the system 100 detects a pathological cardiac event it automatically performs a predefined action. These predefined actions can include: (1) raise a sound alarm on the PDA, i.e., to stop the exercise, or to wake up the patient, etc.; (2) send a relevant ECG signal fragment with an analysis report to a server for further analysis; (3) send a diagnosis confirmation; (4) archive the event; and/or (5) store the ECG fragment and analysis report on the PDA memory card for later reference.

The system 100 provides ECG detecting arrhythmias and ST segment elevation monitoring, QT segment duration monitoring and TWA amplitude monitoring with automatic analysis and pre-selection of pathological events. The system 100 selects and immediately sends these ECG tracing intervals where an abnormal event took place. The system 100 is also effective during the night, when the patient does not feel any symptoms, or during daytime asymptomatic (but potentially important) events, which may occur during the tele-rehabilitation exercises, or between the exercise sessions.

The system 100 allows for simultaneous monitoring and controlling of the tele-rehabilitation progress of larger number of patients at the same time, due to effective automated events detection in real-time. It is also possible to configure the system 100 to periodically send an ECG segment, even if no pathologies are detected, or to provide ECG on demand by a requesting physician (any ECG fragment can be requested by a doctor).

The microcomputer based software running on the PDA 120 is responsible for managing wireless communication with the ECG transmission/acquisition unit 126; managing ECG analysis data exchange via mobile telephone network 132 with the server 136 application (directly) and with the desktop 142 based client application (indirectly—through the server application); initializing patient examination; initializing tele-rehabilitation exercise sessions, guiding the patient through the exercises and providing heart rate information in real-time to allow the patient to control the exercise intensity; introducing patient condition related data before each tele-rehabilitation exercise session; managing patient condition related data exchange via mobile telephone network 132 with the server 136 application (directly) and with the desktop 142 based client application (indirectly— through the server application); storing and managing ECG data; visualizing, in real-time, the ECG waveform, annotations, ST segment elevation, QT interval, TWA amplitude and other parameters; viewing and analyzing recorded ECG signals; generating analysis reports; displaying text and graphical messages, which describe the examination status; examination time; microcomputer battery status; ECG acquisition/transmission unit battery status; wireless connection status; text messages obtained from the server (i.e., messages from a physician); other information related to the examination; configuring the ECG analysis algorithms; configuring events and actions; and configuring tele-rehabilitation program, enabling the patient to manually send the current ECG fragment to the server (i.e., and to the physician's desktop computer).

The desktop based software running on the desktop 142 is responsible for direct synchronization (via e.g., USB cable) with the microcomputer 121 to initialize the examination and link the patient's personal data with the examination ID generated by the microcomputer software; set/edit the examination settings (e.g., tele-rehabilitation program, ECG analysis settings, events settings and action settings); finalize the examination and link the patient personal data with the examination ID (in case of remotely initialized examinations); HL7 data editing and management; visualization of ECG signals with annotations obtained from the server (i.e., the signals and annotations are submitted to the server, during the examination by the microcomputer in real-time); present the patient condition describing information, submitted by the patient before each exercise session; remote triggering of the exercise guiding software running on the patient's PDA 120; remote configuration of the examination settings on the PDA 120 (through the server application); sending text and/or graphical messages to the PDA 120 screen display (via the server application), for instance to inform the patient to take a specific medication, to modify the medication dose, or to check the electrodes, which may not be well attached to the patient's body, etc.; inform the user (e.g., physician) of incoming ECG fragments from the monitored patients; manage the recordings (examinations), such as adding; removing; editing; report generation; ECG and annotation visualization; events based navigation through the entire examination; report based navigation through the entire examination; and navigating through the entire examination based on trends and auxiliary information.

In some embodiments, server software is responsible for data exchange between the PDA 120 carried by the patient (responsible for managing the tele-rehabilitation and for analyzing the ECG in real-time, beat-by-beat) and the desktop computer or control module 142 used by the doctor/physician/operator (for reviewing the analysis results and remote programming the monitoring analysis algorithms and the tele-rehabilitation program and controlling the tele-rehabilitation progress and patient condition, for viewing the examination progress, the incoming ECG fragments, annotations describing detected arrhythmias, beat classification, QT interval duration, ST segment elevation, TWA amplitude and other auxiliary information, for editing the results, approving the diagnosis, etc.). The server application gathers data submitted by the microcomputer 121 (via the mobile telephone network 132) and stores it in a database for the physician to access from his/her desktop 142. The data may contain event description, event priority, event types, etc. Similarly, all information provided by the physician's desktop application for the PDA microcomputer 121 (patient's) application is managed by the server application.

The communication procedure, i.e., communication between the PDA microcomputer 121 application, responsible for constant monitoring and analysis of the patient's ECG and the desktop visualization/editing application operated by the physician on the desktop computer 142, has been designed to allow the doctor to efficiently monitor a large group of patients at the same time (Communication scheme of FIG. 1). This effect is achieved by pre-selection (filtering) and auto-analysis of the information before it is presented to the specialist. The filtering and analysis is performed using ECG analysis algorithms operating on the patient's PDA 120 or microcomputer 121. Embedding the ECG analysis algorithms on the microcomputer has additional benefits. In case of limited (insufficient) bandwidth of the mobile telecommunication network, unnecessary data (i.e., normal ECG signal) is not sent to the physician or monitoring specialist.

It is important to note that all information describing every ECG beat, such as TWA amplitude (for each lead); QT interval; similarity of each T wave to the reference T wave used for QT interval changes calculations; beat type; QRS location in time; arrhythmia type; ST segment elevation (for each lead); similarity to averaged PQRST complex; ADC network interference level (for each lead); and broad band noise level (for each lead) are transmitted to the server (and are available at the desktop application). Such a set of parameters has been carefully chosen to enable, even without viewing the accompanying ECG waveform, discriminating between clean ECG and misclassified artifacts. In case of doubts, the desktop application interface allows for requesting any ECG fragment. This allows the physician access to any ECG fragment stored in the microcomputer 121 memory at any time (such a request message is submitted to the microcomputer 121 application via the server application, and the requested ECG fragment is immediately returned to the server for further analysis.

This set of parameters, also allows for very quick navigation through very long ECG recordings, and for simultaneous management of many patients by one trained specialist. The information set is also sufficient to generate daily reports, generate ECG analysis statistics, etc.

Another important feature of the communication procedure is the interactivity of the system, available during the examination. The physician, using of his/her desktop 130 application can re-configure tele-rehabilitation program, re-configure the ECG analysis algorithm (if the algorithm is too sensitive to artifacts, or not sensitive enough to slightly varying ECG multi-forms, etc), re-configure event settings, action settings and other settings of the microcomputer application, request any ECG fragment (as explained earlier), or send text and graphical messages to the patient (to e.g., change medications, to replace electrodes, or to request contact with the monitoring center, etc.) at any time. Moreover, the doctor may manually correct algorithm findings (manually supervise algorithm training with the desktop application, based on the received data) and remotely provide the Microcomputer, running the analysis algorithms, with the training adjustments. In another example, the patient may decide to manually send ECG fragment to the doctor (perceived symptom based event), or request a telephone contact by simply taping an appropriate button on the microcomputer touch-screen.

Figure 4:
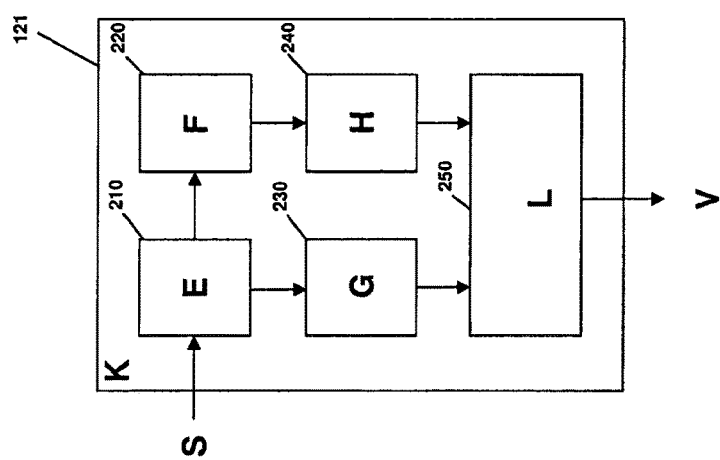
FIG. 4 is a schematic illustration of a device for performing a lead-limited ECG signal analysis.

FIG. 4 schematically illustrates an embodiment of the processing module 121 for the lead-limited ECG signal analysis. The processing module 121 includes a DC removal unit 210, a signal pre-processing unit 220, a detection and evaluation unit 230, an arrhythmia detection unit 240, and a final processing unit 250. In some embodiments, these units (210-250) may be facilitated in hardware of the processing module 121 or software of the analysis module 122.

In operation, the ECG signal "S" obtained from a patient is input into the processing module 121. From the DC removal unit 210, the signal enters into the signal pre-processing unit 220 responsible for performing the signal pre-processing, QRS detection and beat classification. From the signal pre-processing unit 220, the signal is provided to the arrhythmia detection unit 240, that is responsible for arrhythmia detection according to predefined logic rules utilizing expert systems. In particular, the expert systems may employ neural networks, fuzzy logic, statistical methods, etc. At the same time, the signal from the DC removal unit 210 is provided to the detection and evaluation unit 230, where detection evaluation, noise and distortion detection, as well as auxiliary information calculation is determined. Signals from the detection and evaluation unit 230 and the arrhythmia detection unit 240 are then fed to the final processing unit 250, which includes preparation of information "V" in a user-readable format.

Figure 5:
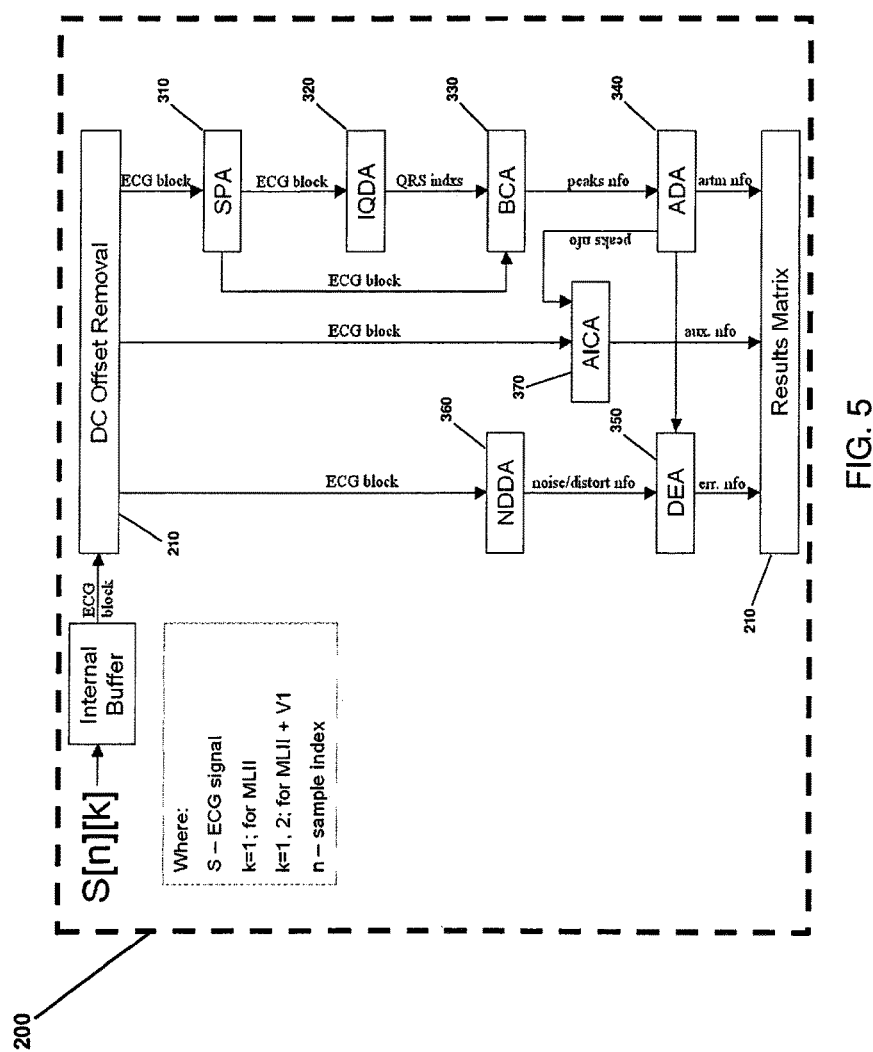
FIG. 5 is a flow-chart of an embodiment of a lead-limited ECG signal analysis algorithm.

FIG. 5 a flow-chart 300 of an embodiment of a lead-limited ECG signal analysis algorithm, where a signal S[n][k], k-representing number of leads is subject to the number of processing steps. The algorithm includes the following functional sub-algorithms or blocks: a signal pre-processing algorithm (SPA) 310; a QRS detection algorithm (IQDA) 320; a beat classification algorithm (BCA) 330; an arrhythmia detection algorithm (ADA) 340; a detection evaluation algorithm (DEA) 350; a noise and distortion detection algorithm (NDDA) 360; and an auxiliary information calculation algorithm (AICA) 370.

The Signal Pre-processing Algorithm (SPA) 310 is responsible for AC interference elimination which is performed by a digital IIR notch filter. The module also removes DC offset and ultra low frequency baseline drift, utilizing delay free linear phase filtering routine, originally developed for the purpose of this application. The routine can be described in the following steps: signal is divided into overlapping blocks; block sizes are related to the averaged heart-rate (HR); mean value of each block is calculated and subtracted for that block; and the ECG signal is reconstructed by cross-fading the successive segments.

Eq. 1 presents on embodiment of a base line correction algorithm for pth ECG segment:

$$y_p[l] = s_p[l] - \frac{\sum_{k=l-L_p/2}^{l+L_p/2} s_p[k]}{L_p} \quad (1)$$

where:
sp—input signal segment;
yp—output signal block;
p—segment index;
l, k—sample indices; and
Lp—pth block size (HR dependent).

The output ECG is constructed from overlapping blocks weighted by a cross-fading window:

$$y[n] = \Sigma_{p=1}^P y_p[l] \cdot w[l] \quad (2)$$

where:
y—output signal;
yp—output signal in pth block;
n, l—sample indices; and
L, N—block size and signal length consequently.
w—cross fading window, e.g., any suitable function of the generalized cosine windows:

$$w[n] = A - B \cdot \cos\left((n-1) \cdot 2 \cdot \frac{\pi}{n-1}\right) + C \cdot \cos\left((n-1) \cdot 2 \cdot \frac{\pi}{n-1}\right) \quad (3)$$

where:
N—window size; and
A, B, C—definable constants.

The presented approach is computationally effective, does not disturb phase of the processed signal and does not introduce oscillatory distortions (so called Gibb's effect) to the processed signal.

Further, QRS detection is performed by statistics based methods in an Intelligent QRS Detection Algorithm (IQDA) 320, which is utilizing information about average HR, higher order statistics description of the rhythm evolution, QRS complexes properties, such as shape and amplitude, T wave shape, base line behavior, noise level and many others, providing very robust decision results. The non-linear prediction of evolving HR (calculated for each beat) allows for calculating the expected QRS time-domain position. This information combined with peak shape analysis and peak level versus surrounding noise level analysis allow for robust QRS complexes detection. Peaks shape analysis and noise level estimation are further described in the BCA block 330 description and the NDDA block 360 description.

Next, a Beat Classification Algorithm (BCA) 330 is used. Based on feature vector (FV) containing description of currently analyzed beat, statistical classifier and ANN system (Artificial Neural Network) performs classification with accordance to peak shape, width, amplitude, T-wave shape, and with reference to previously calculated feature vectors representing reference normal beats, reference pathological beats and as well as recently classified beats. After primary recognition, BCA performance is evaluated with reference to multidimensional prediction coefficients, describing evolution of the feature vectors. Based on the Euclidean distance between predicted FV and measured FV, unpredictability measure parameter for the current beat is estimated and primary recognition improved. The peak shape description parameters are obtained from a preprocessed ECG block. The preprocessing routine is based on a linear operations utilizing moving average filter bank and difference function. In one embodiment, the preprocessing is performed in the following steps:

$$v_1[n] = \frac{1}{K} \sum_{k=n-K/2}^{n+K/2} y[k] \quad (4)$$

$$v_2[n] = \frac{1}{l} \sum_{l=n-L/2}^{n+L/2} v_1[N-l+1] \quad (5)$$

$$v_3[n] = \frac{1}{l} \sum_{l=n-L/2}^{n+L/2} v_2[N-l+1] \quad (6)$$

$$y'[n] = v_3[n] - v_1[n] \quad (7)$$

where:
N – signal length;
$K = \lfloor \frac{fs}{25} \rfloor$;
$L = \lfloor \frac{fs}{50} \rfloor$; and
fs – sampling rate.

Figure 6:
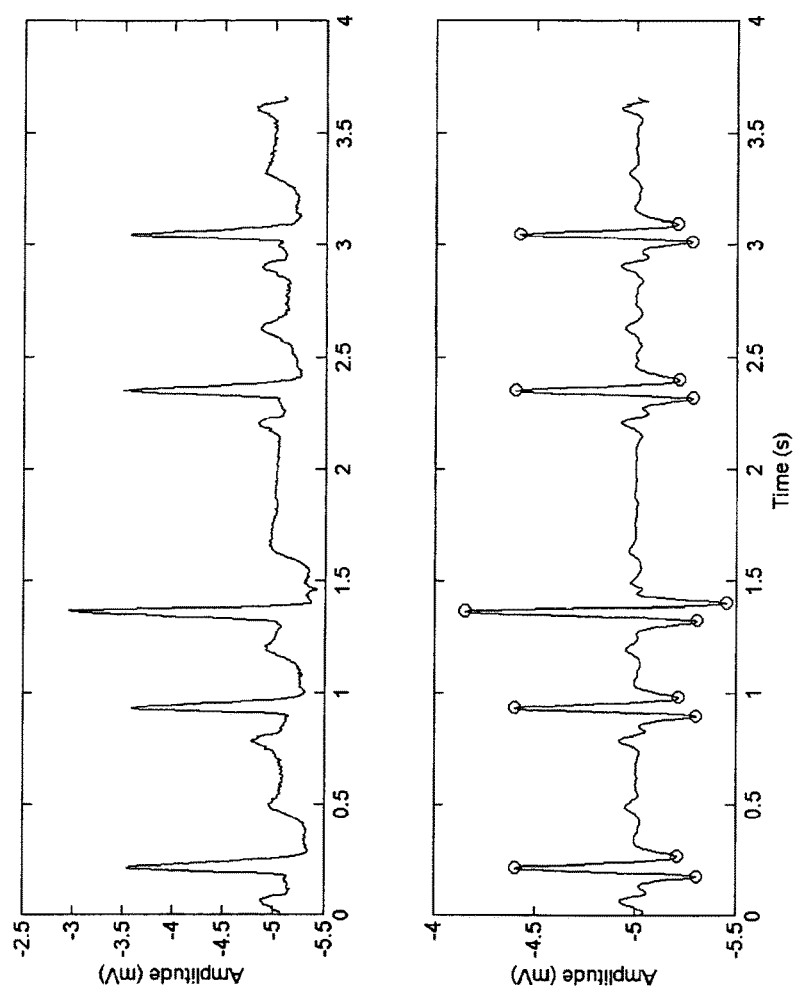
FIG. 6 is a graph of an input signal (upper) and preprocessed signal with regard to Equations 4-7 (lower)

FIG. 6 presents the input (upper part of the figure) and the preprocessed signals with regard to Equations 4-7. Difference ratios of the local extremes, marked by circles, related to each QRS complex are used in the FVs as peak shape descriptors.

Figure 7:
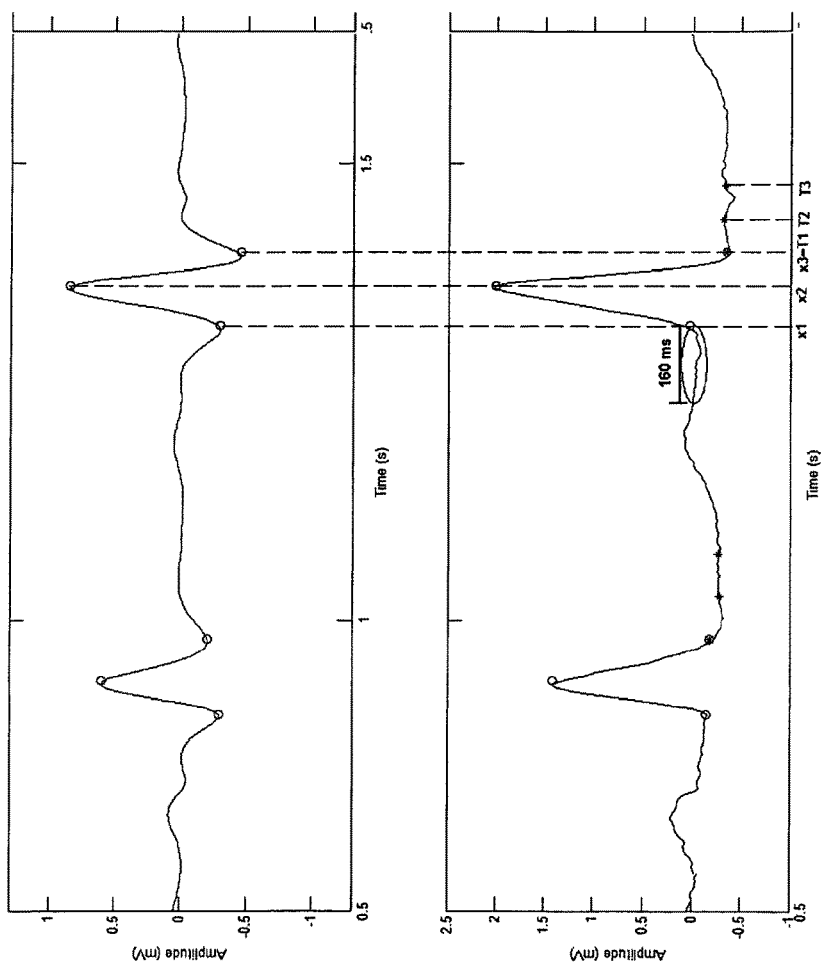
FIG. 7 is a graph of local extremes and T wave shape calculation points.

The peak width (also used in FVs) is obtained by calculating a difference between the left and the right index of the local extremes for each beat (left and right peak marked by circle, for each QRS complex consequently, e.g., x3-x1 in FIG. 7). In addition, auxiliary width calculation algorithm, operating in the frequency domain, is used. In the first step of this method derivative of a smoothed ECG (v1 from Eq. 4) is calculated, i.e.:

$$dv_1 = v_1[n+1] - v_1[n] \quad (8)$$

Then, 400 ms regions surrounding each QRS complex are transformed into frequency domain with the use of FFT algorithm. In practice, the number of samples representing the analyzed region is rounded to the nearest power of two for computational efficiency, i.e.:

$$N = 2^{round(log_2(0.4 \cdot fs))} \quad (9)$$

where:
fs—sampling rate,
N—FFT order,
round( . . . )—rounding to the nearest integer towards zero.

The spectrum based width is obtained in the following way:

$$w = 2 \cdot \left(\frac{N}{2} + 1\right) / \frac{\sum_{n=1}^{N/2} |X[n]| \cdot n}{\sum_{n=1}^{N/2} |X[n]|} \quad (10)$$

were:

w—spectrum based QRS complex width,
N—FFT size (analyzed region size),
X—complex spectrum of the derivative of a smoothed ECG (dv1).

The parameters describing T wave shape (also utilized in the Feature Vectors), are obtained with regard to the local extremes time position (See FIG. 4 and also x1, x2, x3 in FIG. 7).

T1, T2 and T3 points are calculated in the following way:

$T1 = x3;$ $T2 = x3 + (x3 - x2);$ and $T3 = x3 + 2*(x3 - x2).$

Values representing T wave shape are base line compensated ECG values for T1, T2 and T3 time instances. The baseline compensation is obtained by subtracting median value of the ECG fragment preceding by 160 ms the x1 point.

It must be stressed that each detected QRS complex is described with such a set of parameters and based on neighbor QRS complexes similarity, measured with an Euclidean distance of the FVs and rhythm properties (considering only non-premature beats) reference normal FVs are obtained, and kept in the N set. All calculated FVs, during the real-time processing are compared to FVs from N set and classified as normal (if similar to any FV from N) or potentially pathological or unknown beats. The potentially pathological or unknown beat FV s are kept for further reference in the P set. In case of newly calculated FV not similar to the reference FVs from N, but similar to one, or more FVs from P, it is classified as pathological. Otherwise (if not similar to any FV from P nor N) it is classified as unknown. Since the P and N sets are constantly updated, the algorithm has ability to learn and adopt to changing conditions.

Further, an Arrhythmia Detection Algorithm (ADA) 340 is utilized. After beats classification, ADA 340 performs arrhythmia detection with accordance with the predefined logic rules as shown below, however similarly to BCA 330 primary recognition process, the decision making module in ADA 340 is based on statistical classifier which adaptively (to the rhythm behavior) performs classification task. The ADA 340 algorithm monitors HR changes, and in case of rapid heart rate increases (assuming sufficiently high BPM) recognizes tachycardia rhythms. In case of chaotic rhythm, assuming sufficient similarity of consecutive beats, a trial fibrillation is detected.

Next, a Detection Evaluation Algorithm (DEA) 350 is employed. Beat recognition and arrhythmia detection is performed for all fragments (even extremely distorted) of the ECG signal. In some cases, however, distortions and noise level may cause misclassifications. Based on the base line drift fluctuations, calculated with the use of 160 ms ECG fragments preceding x1 point for each QRS complex (see FIG. 7), distortions are detected. Also noise level, nonlinear distortion disturbances (hard clipping) and neighbor similarity of consecutive QRS complexes (calculated with regard to FV s used in BCA 330) are used as a signal condition descriptor.

At the same time, a Noise and Distortion Detection Algorithm (NDDA) 360 is used for detecting non-linearly distorted ECG fragments, usually caused by hard clipping. The detector analyzes consecutive samples, and in case of identical values over and under predefined maximum and minimum threshold, detects the distortion. In addition a broad band noise energy is estimated with the use of Unpredictability Measure (UM) algorithm. The UM algorithm is very much suitable for ECG analysis, because the electrocardiographic signal is quasi-periodic (similarly to audio signals) and chaotic phase of the spectrum components is related to parasite noise. UM is calculated in the following way:

$$\alpha_k^t = \frac{\sqrt{\left(r_k^t \cdot \cos\Phi_k^t - \hat{r}_k^t \cdot \cos\hat{\Phi}_k^t\right)^2 + \left(r_k^t \cdot \sin\Phi_k^t - \hat{r}_k^t \cdot \sin\hat{\Phi}_k^t\right)^2}}{r_k^t - |\hat{r}_k^t|} \quad (11)$$

For $r_k^t$ denoting spectral magnitude and $\Phi_k^t$ denoting phase, both at time t, while $\hat{r}_k^t$ and $\hat{\Phi}_k^t$ represent the predicted values of $\Phi_k^t$, and are referred to the past information (calculated for two previous signal sample frames):

$$\alpha_k^t = \begin{cases} \hat{r}_k^t = r_k^{t-1} + (r_k^{t-1} - r_k^{t-2}) \\ \hat{\Phi}_k^t = \Phi_k^{t-1} + (\Phi_k^{t-1} - \Phi_k^{t-2}) \end{cases} \Rightarrow \begin{cases} \hat{r}_k^t = 2 \cdot r_k^{t-1} - r_k^{t-2} \\ \hat{\Phi}_k^t = 2 \cdot \Phi_k^{t-1} - \Phi_k^{t-2} \end{cases} \quad (12)$$

Figure 8:
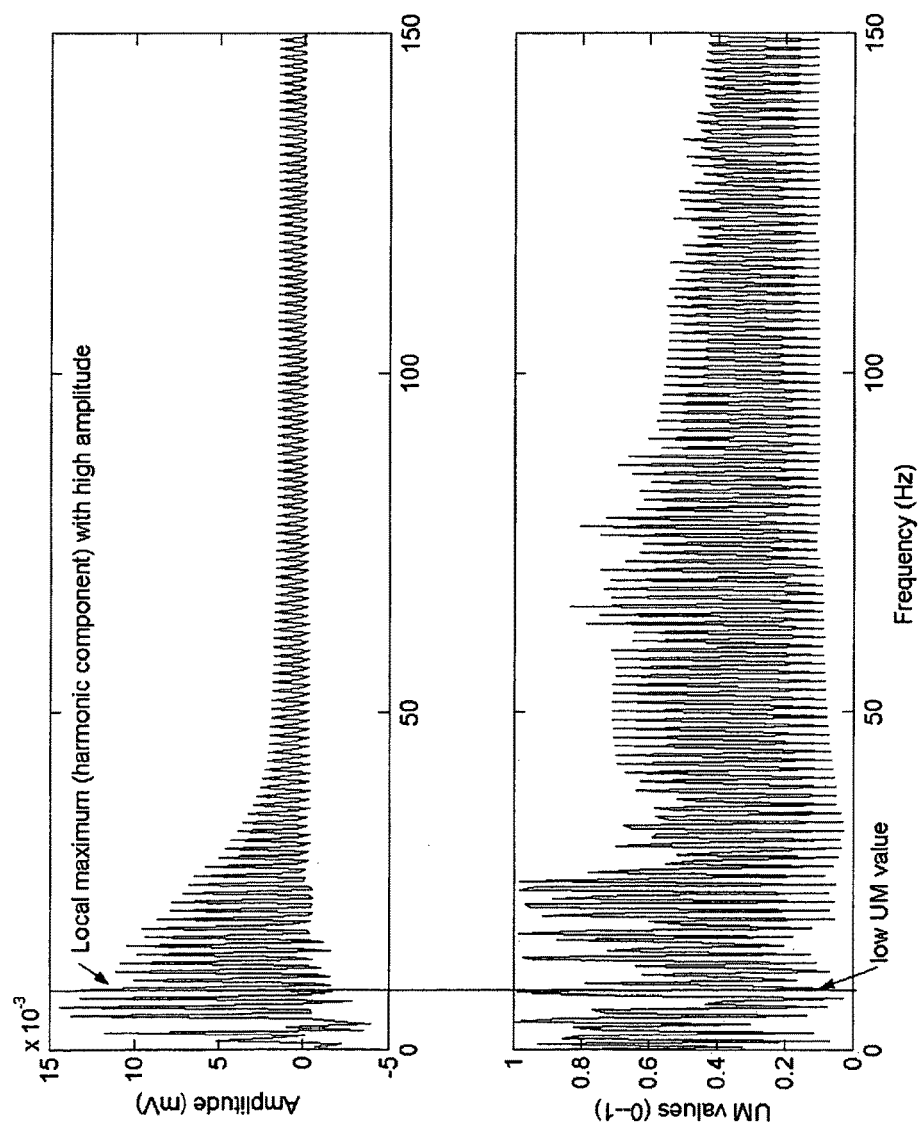
FIG. 8 is a graph of a clean ECG spectrum (upper) and an Unpredictability Measure (UM) graph (lower)
Figure 9:
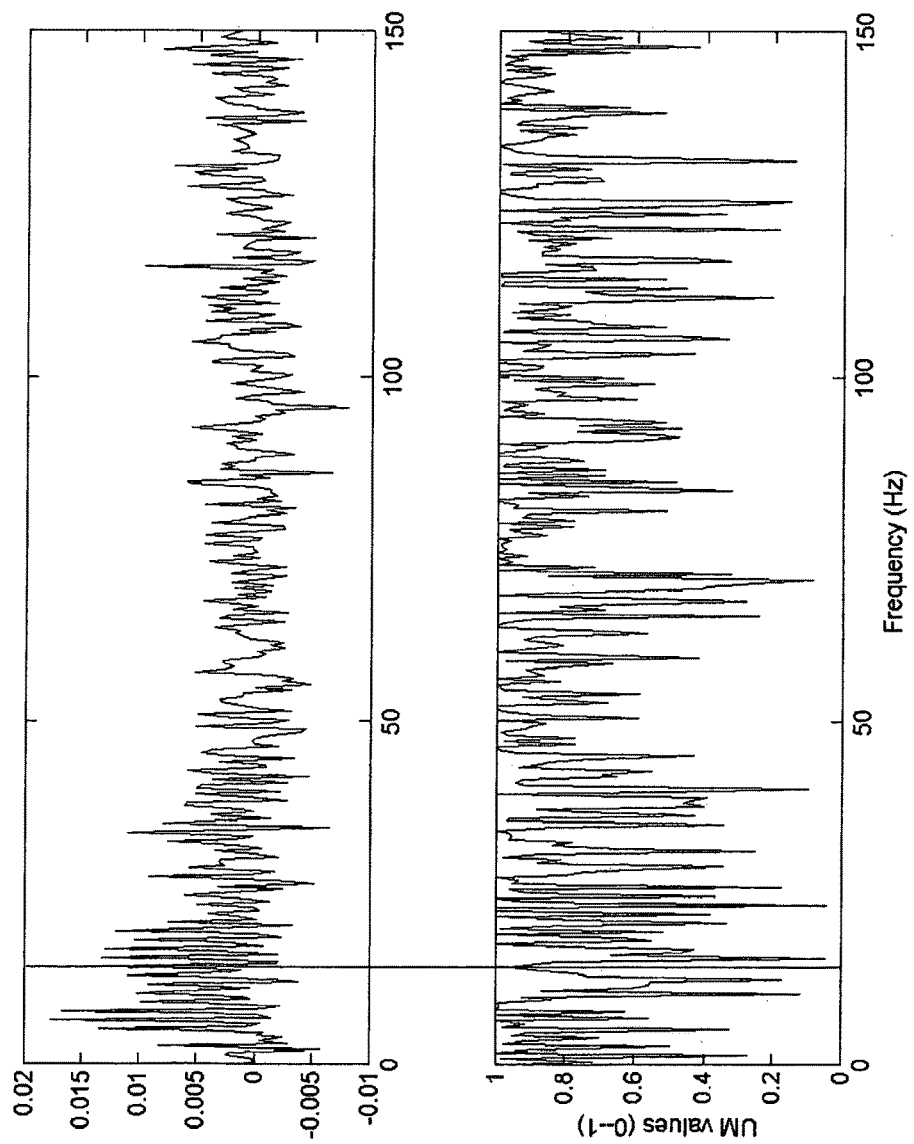
FIG. 9 is a graph of a noisy ECG spectrum (upper) and a UM graph (lower)

Spectrum of three consecutive periods of ECG is shown in upper part of FIG. 8. UM graph obtained from that spectrum and two previous sample frames is shown in the bottom part of FIG. 8. Spectrum and UM, consequently, of the same signal but contaminated with artificially added Gaussian white noise are presented in FIG. 9. It can be observed that local maxima of the spectrum from FIG. 6 correspond with the local minima (low UM values) from the figure. While in noisy signal, presented in FIG. 9, high magnitude level of the spectrum bins do not correspond with low UM values in bottom part of the figure.

Since the sinusoidal components in a clean quasi-periodic signal usually carry the most energy of the signal and the UM values of such components are near zero, the UM weighted noise energy estimate for time t is calculated in the following way:

$$E^t = \left(1 - \frac{\sum_{k=1}^{K}(1 - \alpha_k^t) \cdot |X_k^t|^2}{\sum_{k=1}^{K} |X_k^t|^2}\right) \cdot \sum_{k=1}^{K} |X_k^t|^2 \quad (13)$$

where:
X—ECG block spectrum,
t—time instance,
k—spectrum bin index,
E—noise energy estimate.

An Auxiliary Information Calculation Algorithm (AICA) 370 is employed as well. AICA module 370 is responsible for calculating average HR, irregularity indicator and HRV, ADC interference level, ST elevation, QT interval and TWA amplitude.

The ST level, QT interval calculator analyze periods similarity and only for properly classified complexes produce the ST deviation and QT interval results, based on an averaged ECG period. The similarity calculation utilizes smoothed ECG (v1 from Eq. 4) and it can be expressed as:

$$S = \frac{\sum_{k=1}^{K} |p_1[k] - p_2[k]|^2}{\sum_{k=1}^{K} p_1[k]^2} \tag{14}$$

where:
S—similarity,
p1, p2—ECG periods,
K—ECG period size.

If S is below predefined similarity threshold, than p 1, p2 are used for updating the averaged ECG period. The averaged period is updated in a recursive way:

$$P_{avg} = \frac{P_{avg} \cdot (K-1) + p_{new}}{K} \tag{15}$$

where:
Pavg—averaged ECG period,
pnew—new ECG period (for S from Eq. 14 below predefined threshold),
K—averaging order.

Figure 10:
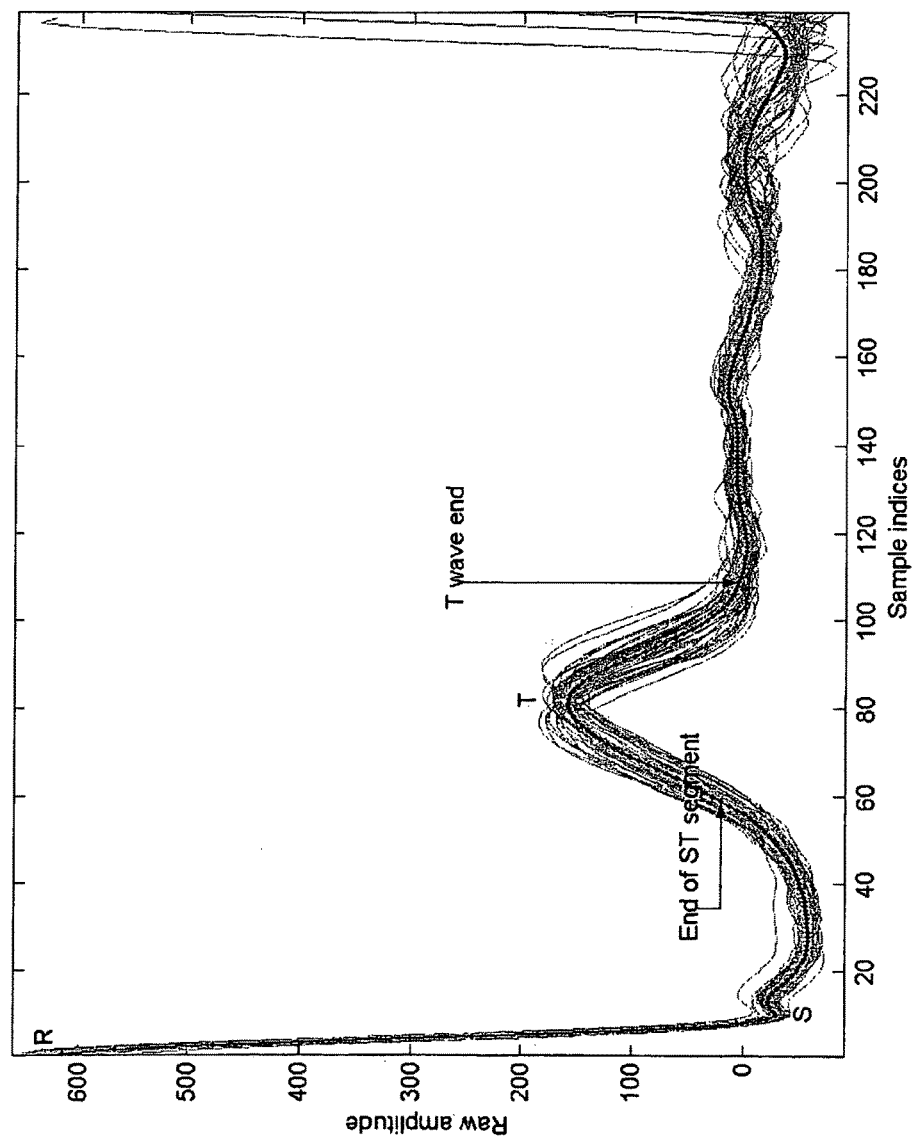
FIG. 10 is a graph of an averaged ECG period used for ST and QT calculations.

Using averaged ECG period for ST segment elevation, QT interval calculations allows for decreasing noise influence and results in robust T wave analysis. Averaged ECG period (black dotted line) vs periods used for calculating the Pavg (gray solid lines) are presented in FIG. 10.

Many of the QT interval measurement algorithms detect T wave end and the beginning of isoelectric baseline for each ECG period. Since the baseline is often disturbed with parasite noise, low frequency disturbances of non-stationary character, these methods assume high quality of the analyzed signal fragment, hence can be utilized only in resting ECG. Many studies show that multi-channel (preferably 12 lead) ECG has to be utilized in order to optimally determine the T wave end. The presented approach is indirect and requires only single determination of QT interval at the beginning of the monitoring session, which can be done manually with the use of 12 lead ECG. The initial QT interval determination also results in extracting reference ECG period and reference T wave, which will be utilized for estimating QT intervals of each non-pathological beat. In fact, the algorithm calculates QT interval variability with regard to the reference T wave and since the reference QT interval is known, all other QT intervals can be determined. The time domain T wave shift is calculated with the use of modified AMDF (Average Magnitude Difference Function) technique, i.e., it is in fact inverted and normalized ASDF (Average Squared Difference Function). Both are popular methods used in speech processing.

Unlike the method which utilizes the time altered (stretched) time domain representation of the T wave, the invented algorithm utilizes time domain shifted difference signal of the T wave. Such an approach is more suitable, because the stretching (deformation) factor of the T wave is unknown, and may vary for different individuals' ECG resulting in inappropriate matching of the T wave decaying slope (i.e., T wave end). Since the attack phase of the T wave (i.e., energy increase at the beginning of the T wave) is less rapid than the energy decay of the T wave, therefore the difference signal around the decaying slope has the highest energy, hence the matching function has the maximum value for the time domain shift matching the decaying slopes. Using the difference signal also eliminates baseline level influence and the influence may affects similarity calculations carried out by the matching function, when processing not filtered ECGs. It must be stressed that standard (IIR or FIR) high pass filtering should not be applied here for the baseline elimination due to influence of the so called Gibbs effect (oscillatory deformations) on the baseline segment which may occur after the T wave end, and may result in erroneous QT interval variability calculations. The T wave matching function of the invented algorithm can be expressed in the following way:

$$p[n] = 1 - \frac{\sum_{k=n-N+1}^{n} (s_1[k] - s_1[k-1]) - (s_2[k] - s_2[k-1])^2}{\sum_{l=N-n+1}^{2 \cdot N-n} \frac{(s_1[l] - s_1[l-1]) - (s_2[l] - s_2[l-1])^2}{4}} \tag{16}$$

where:
p—matching curve of the time domain shifted T wave difference signals,
N—number of samples of the compared T waves,
n=1, . . . , 2·N−1
$s_1$, $s_2$—compared T waves.

Figure 11A:
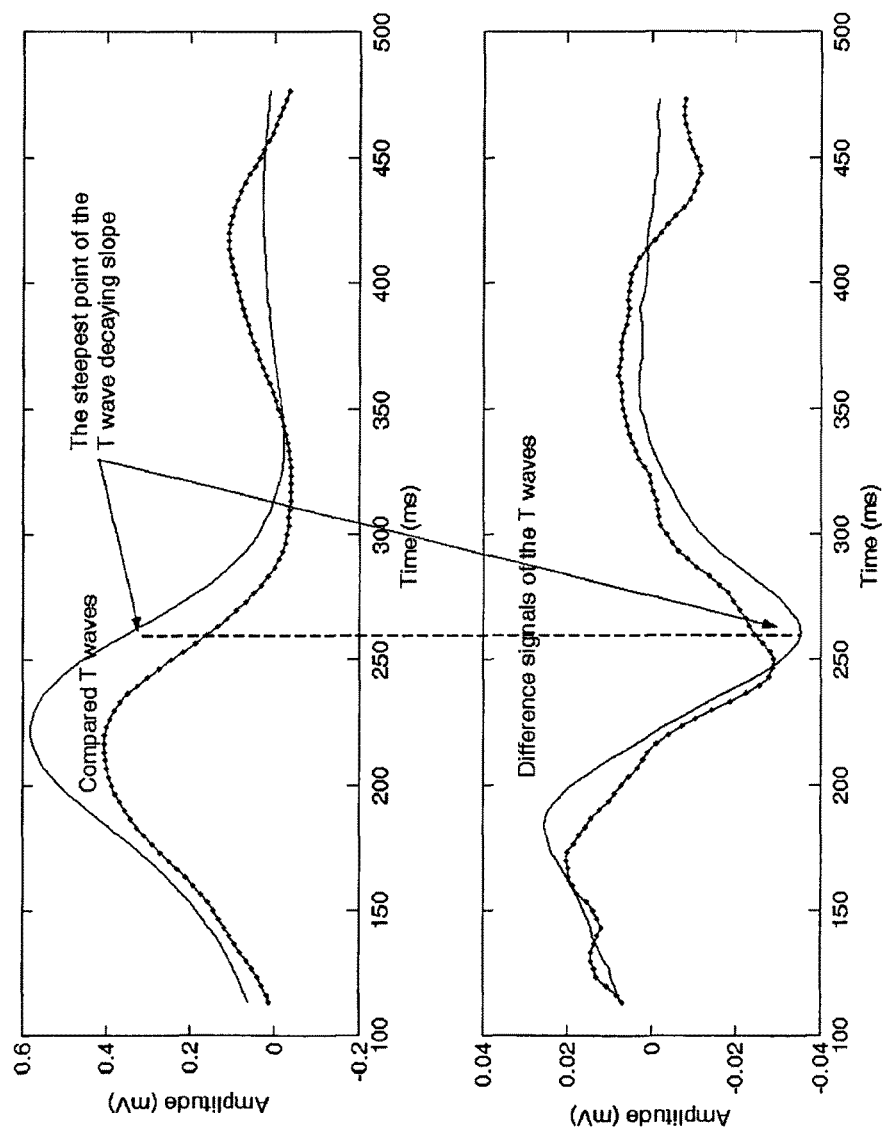
FIG. 11A shows a new T wave (dotted) and a reference T wave (solid) in upper part of the figure and the bottom part of the figure presents difference signals of the new T wave (dotted) and difference signal of the reference T wave (solid)

It must be stressed that the compared ECG periods are in fact recursively averaged (see Eq. 15) periods. Averaging allows for decreasing influence of the parasite noise and parasite disturbances. Upper part of FIG. 11A presents the reference ECG period (solid line) vs new period (solid/dotted line), while bottom part of the figure shows difference signals of the T waves. T wave time shift is easily distinguishable in the figure, however T wave end for the new period would be impossible to mark, due to the P wave close presence. Utilizing the proposed method allows for prediction (based on the similarity of the reference T wave and the analyzed new T wave) of the QT interval.

Figure 11B:
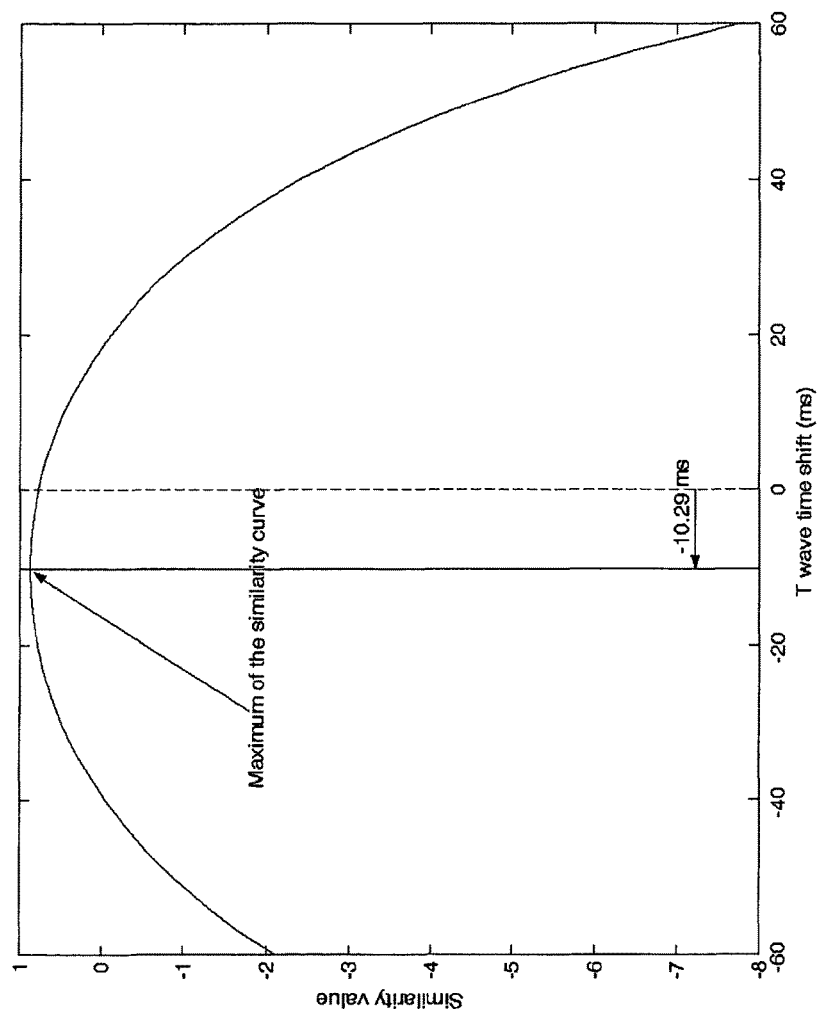
FIG. 11B is a similarity curve of a time domain shifted difference signals of the example T waves from FIG. 11A.

FIG. 11B shows the similarity curve with regard to Eq. 16, presenting the time shift influence of the compared T wave representations (i.e., the T wave signals from the bottom part of FIG. 11A). Applying parabolic interpolation on the similarity curve, i.e., fitting parabola to the maximum sample and the surrounding samples allows for achieving T wave shift accuracy significantly exceeding the ECG signal sampling rate limitations:

$$\begin{cases} c = v_{max} \\ b = \frac{v_R - v_L}{2} \\ a = v_L + \frac{v_R - v_L}{2} - c \end{cases} \tag{17}$$

$$l_{dv} = \frac{-b}{2 \cdot a}$$

$$\hat{\imath}_{max} = i_{max} + l_{dv}$$

where:
$v_{max}$—value of the maximum sample of the similarity curve, $v_L$, $v_R$—value of the left and right sample surrounding the maximum,
$I_{dv}$—correction value of the maximum sample index,
$i_{max}$—index of the maximum sample of the similarity curve,
$i_{max}$—approximated index with the use of parabolic interpolation.

It is important to mention that the T wave shape may change over time. In most of the cases the reason for the shape evolution is changing heart rate, where the T wave amplitude and duration adopts to the cardiac cycle duration. Also, in case of significant ST segment elevation episodes, or in case of T wave alternans episodes, or body position changes, etc. the T wave shape may also evolve over time. Therefore, to efficiently deal with such situations and in order to avoid comparison of the reference T wave selected at the beginning of the examination, with the new T waves of significantly different shape, auxiliary T wave reference signals are automatically collected during the processing. When the reference T wave and the currently processed new T wave similarity value is below predefined threshold, and also if the new T wave and its N preceding T waves similarity value are above the predefined threshold, than the new processed T wave becomes a new auxiliary reference T wave. The similarity values are calculated in the following way:

$$d_{sim} = 1 - \frac{\sum_{n=1}^{N}(s_{ref}[n] - s_{new}[n])^2}{\sum_{n=1}^{N}\frac{(s_{ref}[n] - s_{new}[n])^2}{4}} \quad (18)$$

where:
$d_{sim}$—similarity value of the compared T waves,
N—number of samples of the compared T waves,
$s_{ref}$—reference T wave signal,
$s_{new}$—new T wave signal.

Thus, the initial reference T wave and the gathered auxiliary T waves form a reference T wave set, consisting of K signals. For each new T wave and all K references $d_{sim}^k$ values are obtained:

$$d_{sim}^k = 1 - \frac{\sum_{n=1}^{N}(s_{ref}^k[n] - s_{new}[n])^2}{\sum_{n=1}^{N}\frac{(s_{ref}^k[n] - s_{new}[n])^2}{4}} \quad (19)$$

Maximum value of $d_{sim}^k$ is treated as the new T wave similarity to the reference T wave signal and based on this value the decision of updating the reference T wave set is made.

The TWA amplitude calculation algorithm utilizes smoothed, but not averaged ECG periods. Because of the instant character of the phenomenon (i.e., T wave amplitude fluctuates in every second beat) averaged ECG period is not directly used by the algorithm, but it is used for removing slowly varying T wave shape trend. In the first step, however, it is necessary to remove baseline offset from the processed ECG periods:

$$b_i = \text{median}(\{p_i[k], \ldots, p_i[k+L]\}), \text{ for } k \in K \quad (20)$$

where:

$p_i$—current (ith) ECG period,
K—set of indices representing baseline,
$b_i$—current (ith) base line level.

In addition, base line deformation ($bd_i$) is calculated. $bd_i$ is a standard deviation of the base line difference signal of the current and the previous smoothed ECG period:

$$bd_i =, \frac{1}{|K|-1}\sqrt{\sum_{k \in K}\left[(p_i[k] - p_{i-1}[k]) - \frac{1}{|K|}\sum_{k \in K}(p_i[k] - p_{i-1}[k])\right]^2} \quad (21)$$

where:
$bd_i$—current (ith) ECG period baseline deformation,
K—set of indices representing baseline,
|K|—the baseline indices set strength, i.e., the number of the indices.

Figure 11C:
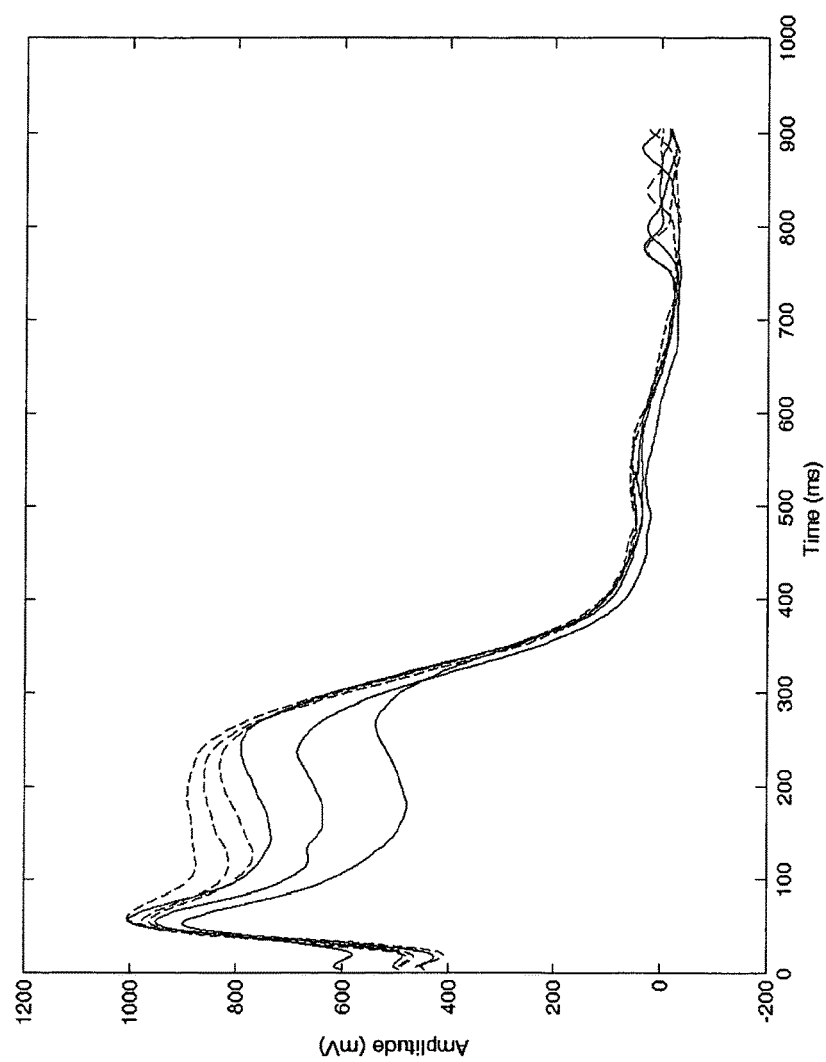
FIG. 11C presents six (6) consecutive ECG periods with TWA present and with a slow T wave shape evolution during a ST elevation event in six (6) consecutive ECG periods.

As mentioned before, the T wave shape may evolve, i.e., it may contain an additive low frequency component related to e.g., ST episodes transient, as presented in FIG. 11C. It can be observed in FIG. 11C, that even periods (solid line) group and odd periods (dashed line) group are not separated. The T wave shape may slowly vary and at the same time TWA might be present. In such situations, analyzing averaged or median even beats versus averaged or median odd beats approach [8] may cause problems. For example, the standard deviations of the two (even and odd) sets may overlap, making the two groups difficult to separate. Therefore the invented algorithm does not separate even and odd ECG periods in two sets, it but analyzes periodicity of the TWA fluctuations, after removing the shape varying trend.

The low frequency trend is removed by subtracting the averaged ECG period from the current ECG period:

$$\bar{p}_i[n] = (p_i[n] - b_i) - \left(\frac{1}{K}\sum_{k=i-K+1}^{i}p_k[n] - b_k\right); \quad (22)$$

$$\text{for } n = 1, \ldots, N$$

where:
N—number of samples of the processed ECG periods,
p—current ECG period,
$\bar{p}$—unbiased, current ECG period,
M—the number of averaged ECG periods,
b—base line level.

Figure 11D:
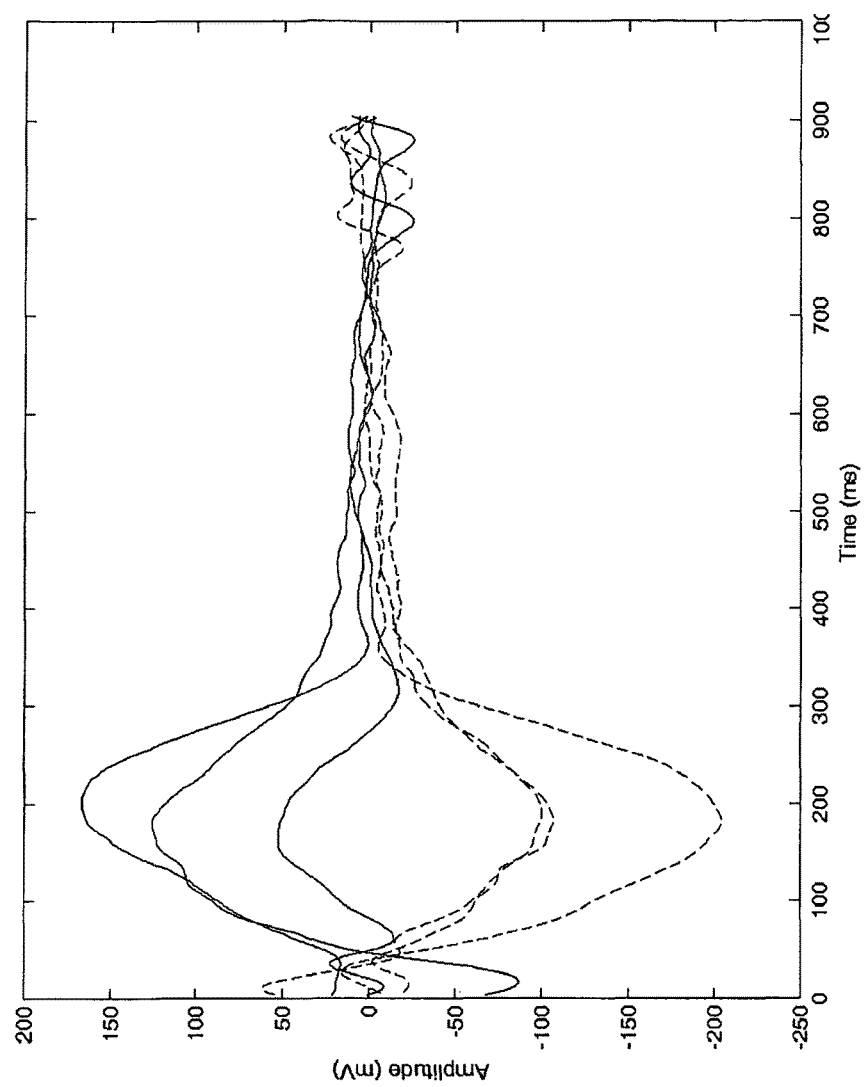
FIG. 11D presents six (6) consecutive unbiased ECG periods with TWA present and with slow T wave shape evolution during ST elevation event in six (6) consecutive ECG periods.

Six (6) consecutive, unbiased ECG periods, i.e., processed ECG periods from FIG. 11C are shown in FIG. 11D. It can be observed in the figure, that even unbiased periods (solid line) group and odd unbiased periods (dashed line) group are well separated.

In the next step, periodicity value describing each sample of the current ECG period, based on L preceding ECG periods is calculated. The periodicity character is calculated based on N autocorrelation sequences.

$$\hat{R}_n[i] = \begin{cases} \sum_{j=1}^{J-i} p_n[j+1] \cdot p_n^*[j], & m \geq 0 \\ \hat{R}_n^*[-i], & m < 0 \end{cases} \quad (23a)$$

$$v_n^1 = 1 - \frac{\sum_{j=1}^{J/2} \left(\hat{R}_n[j \cdot 2 - 1] + \hat{R}_n[j \cdot 2]\right)^2}{\sum_{j=1}^{J/2} \left(\hat{R}_n[j \cdot 2 - 1] + \hat{R}_n[j \cdot 2]\right)^2} \quad (23b)$$

$$v_n^2 = \frac{2}{J/2 - 1} \sum_{j=1}^{J/2-1} \frac{\hat{R}_n[j \cdot 2 + J/2 - 2]}{\hat{R}_n[J]} \quad (23c)$$

$$P_n = v_n^1 + v_n^2 \quad (23d)$$

where:
$\hat{R}_n$—nth autocorrelation sequence
J—the number of periods used for calculating autocorrelation sequences,
n—ECG period index number,
$P_n$—periodicity value.

The unbiased-average-difference-ECG-period signal is calculated as follows:

$$\hat{p}_i = \Sigma_{j=j-J/2} \overline{p}_{j \cdot 2} - \overline{p}_{j \cdot 2 - 1} \quad (24)$$

where:
$\hat{p}_i$—current (ith) unbiased-averaged-difference-ECG-period,
J—the number of periods used for periodicity analysis and for averaging.

Figure 11E:
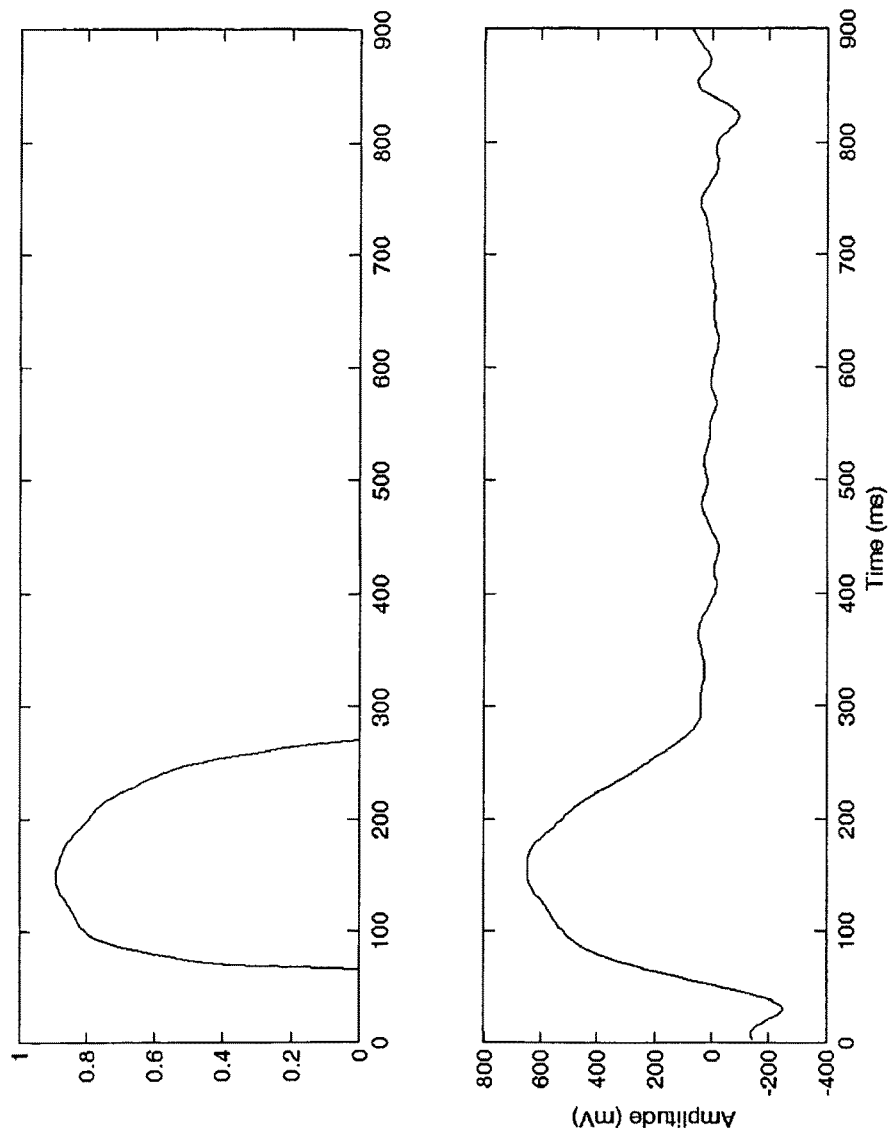
FIG. 11E is an eriodicity curve (upper) and an unbiased-averaged-difference-ECG period (bottom).

The periodicity curve is presented in FIG. 11E (upper part). Unbiased-averaged-difference-ECG-period is presented in the bottom part of FIG. 11E.

Finally, the T wave alternans amplitude of the current (ith) ECG period is the maximum value, obtained for the T wave region in the unbiased-averaged-difference-ECG-period weighted by the periodicity value, and compensated by the base line fluctuations correction value (Eq. 20) and the baseline deformation correction value (Eq. 21):

$$p_{prdc}^i[n] = \hat{p}_i[n] \cdot P_n \quad (25a)$$

$$bc_i =, \frac{1}{J-1} \sqrt{\sum_{j=i-J+1}^{i} \left[b_j - \frac{1}{J} \sum_{k=i-J+1}^{k} b_k\right]^2} \quad (25b)$$

$$A_{TWA}^i = \max_{n \in N^T} (p_{prdc}^i) - (bc_i + bd_i) \quad (25c)$$

where:
$P_{prdc}^i$—current (ith) unbiased-averaged-difference-ECG-period weighted by the periodicity ECG period representation,
$bc_i$—base line deviation,
$N^T$—set of indices related to the T wave region,
$A_{TWA}^i$—current (calculated for the ith ECG period) T wave alternans level.

The algorithm calculates T wave alternans amplitude on the beat-to-beat basis. The method provides very robust results and is resistant to parasite broad band noise and artifacts, because this kind of disturbances affect the periodicity character of the T wave shape fluctuations, hence the periodicity analysis (Eq. 23a-23d) eliminates potentially incorrectly detected T wave amplitude variations. In addition, potentially incorrectly generated T wave level fluctuations produced by parasite base line level drift are compensated by the base line level standard deviation value (Eq. 25b) and the base line deformation value (Eq. 21).

The system 100 (FIG. 1) has ability to adopt to analyzed signal and due to learning procedures and deals effectively with various and different ECG signals. The method operates in real-time and returns information about the detected ECG events.

The T wave related parameters, i.e., ST segment elevation, QT interval duration and TWA amplitude can be calculated only in case of properly detected QRS complexes and correctly classified beats, therefore the QRS detection and classification component and the arrhythmia detection component of the system is of great importance and is the basis for proper T wave analysis. Many arrhythmia recognition, peak classification and auxiliary information algorithm blocks operate on predefined, or adaptively calculated parameters.

The above described systems and methods can be implemented in digital electronic circuitry, in computer hardware, firmware, and/or software. The implementation can be as a computer program product (i.e., a computer program tangibly embodied in an information carrier). The implementation can, for example, be in a machine-readable storage device and/or in a propagated signal, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magnetooptical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer® available from Microsoft Corporation, Mozilla® Firefox available from Mozilla Corporation). The mobile computing device includes, for example, a Blackberry®.

Comprise, include, and/or plural forms of each are open ended and include the listed parts and can include additional parts that are not listed. And/or is open ended and includes one or more of the listed parts and combinations of the listed parts.

One skilled in the art will realize the embodiments may be embodied in other specific forms without departing from the spirit or essential characteristics thereof. The foregoing embodiments are therefore to be considered in all respects illustrative rather than limiting of the embodiments described herein. Scope of the embodiments is thus indicated by the appended claims, rather than by the foregoing description, and all changes that come within the meaning and range of equivalency of the claims are therefore intended to be embraced therein.

What is claimed is:

1. A system for recording and processing ECG signals, the system comprising:
    an ECG digitization and wireless transmission device (ECG_DWT) comprising:
        a single lead configured to record real-time, beat-by-beat, ECG signals, and
        a ECG_DWT transceiver configured to transmit the real-time ECG signals;
    a tele-rehabilitation module comprising:
        an ECG transceiver configured to receive the real-time ECG signals, and
        circuitry configured to i) process the real-time ECG signals and ii) recognize erroneous signals and reduce noise in the real-time, beat-by-beat, ECG signals received from the single lead, and
        wherein the ECG transceiver is further configured to transmit the processed real-time ECG signals to a network; and
    a remote monitoring module comprising:
        a computer periphery device configured to connect to the network and receive the real-time ECG signals and the processed real-time ECG signals, and
        a monitor configured to display real-time waveforms of the real-time ECG signals including the processed real-time ECG signals.

2. The system of claim 1, wherein the module is further configured for constant monitoring and analysis of the patient's ECG signals.

3. The system of claim 1 wherein the ECG transceiver employs a communications protocol designed to allow a specialist to simultaneously monitor a large group of patients.

4. The system of claim 1, wherein the tele-rehabilitation module is further configured to receive patient input to send an ECG fragment related to a perceived symptom based event to a doctor.

5. The system of claim 1, wherein the single lead includes a first electrode and a second electrode.

6. The system of claim 1, wherein the ECG DWT device is also configured to operate on a multi-channel signal that includes signals from three or more electrodes.

7. The system of claim 1, further comprising a control module operable connected to the remote monitoring module and comprising circuitry configured to remotely reconfigure settings of limited lead analysis circuitry operably coupled to the telerehabilitation module.

8. A method for remote recording and processing ECG signals from a patient for transmission to medical personnel, the method comprising:
    recording, using an ECG digitization and wireless transmission (DWT) device real-time, beat-by-beat, ECG signals using a single lead;
    processing, via a tele-rehabilitation module circuitry communicatively coupled to the ECG DWT device, the real-time ECG signals;

recognizing erroneous signals and reducing noise in the real-time, beat-by-beat, ECG signals received from the single lead, via the tele-rehabilitation module circuitry; and displaying, via a monitor of a computing device communicatively coupled to the tele-rehabilitation module, real-time waveforms of the real-time ECG signals including the processed real-time ECG signals.

9. The method of claim 8, further comprising constantly monitoring and analyzing, via the tele-rehabilitation module circuitry, the ECG signals.

10. The method of claim 8 further comprising receiving, via the tele-rehabilitation module, patient input to send an ECG fragment related to a perceived symptom based event to a doctor.

11. The method of claim 8 wherein the single lead comprises a first electrode and a second electrode.

12. The method of claim 8, further comprising recording, using the ECG DWT device, the ECG signals, on a multi-channel signal that includes signals from a multiple leads, the multiple leads including three or more electrodes.

13. The method of claim 8, further comprising remotely re-configuring, via a control module operable connected to the remote monitoring module, settings of limited lead analysis circuitry operably coupled to the tele-rehabilitation module in response to receiving all the gathered information.

* * * * *